(12) United States Patent
Gregg et al.

(10) Patent No.: US 10,792,170 B2
(45) Date of Patent: Oct. 6, 2020

(54) SYSTEMS AND METHODS FOR PROSTHETIC DEVICE CONTROL

(71) Applicant: BOARD OF REGENTS, THE UNIVERSITY OF TEXAS SYSTEM, Austin, TX (US)

(72) Inventors: Robert D. Gregg, Allen, TX (US); David Quintero, Fort Worth, TX (US); Anne E. Martin, Dallas, TX (US); Darío J. Villarreal Suárez, Farmers Branch, TX (US)

(73) Assignee: BOARD OF REGENTS, THE UNIVERSITY OF TEXAS SYSTEMS, Austin, TX (US)

(*) Notice: Subject to any disclaimer, the term of this patent is extended or adjusted under 35 U.S.C. 154(b) by 94 days.

(21) Appl. No.: 15/550,556

(22) PCT Filed: Feb. 11, 2016

(86) PCT No.: PCT/US2016/017453
§ 371 (c)(1),
(2) Date: Aug. 11, 2017

(87) PCT Pub. No.: WO2016/130745
PCT Pub. Date: Aug. 18, 2016

(65) Prior Publication Data
US 2018/0036147 A1 Feb. 8, 2018

Related U.S. Application Data

(60) Provisional application No. 62/115,350, filed on Feb. 12, 2015.

(51) Int. Cl.
*A61F 2/68* (2006.01)
*A61F 2/70* (2006.01)
(Continued)

(52) U.S. Cl.
CPC .............. *A61F 2/70* (2013.01); *A61F 2/60* (2013.01); *A61F 2/68* (2013.01);
(Continued)

(58) Field of Classification Search
CPC ...... A61F 2/68; A61F 2/70; A61F 2/66; A61F 2/6607; A61F 2/72
(Continued)

(56) References Cited

U.S. PATENT DOCUMENTS

2004/0064195 A1* 4/2004 Herr .................... A61F 2/66
623/24
2005/0251079 A1* 11/2005 Garvey .............. A61F 5/0102
602/26

(Continued)

FOREIGN PATENT DOCUMENTS

CA  2876187 A1  12/2013

OTHER PUBLICATIONS

Mace, M et al. "A heterogeneous framework for real-time decoding of bioacoustic signals: Applications to assistive interfaces and prosthesis control" Expert Systems with Applications 40.13: 5049-5060; especially p. 5054. (Mar. 28, 2013) (Year: 2013).*

(Continued)

*Primary Examiner* — Suba Ganesan
*Assistant Examiner* — Aren Patel
(74) *Attorney, Agent, or Firm* — Parker Highlander PLLC

(57) ABSTRACT

Systems and methods for prosthetic device control with a unified virtual constraint that controls an entire gait cycle of the prosthetic device.

55 Claims, 14 Drawing Sheets

(51) Int. Cl.
*A61F 2/60* (2006.01)
*A61F 2/76* (2006.01)

(52) U.S. Cl.
CPC ... *A61F 2002/701* (2013.01); *A61F 2002/704* (2013.01); *A61F 2002/7615* (2013.01); *A61F 2002/7645* (2013.01)

(58) Field of Classification Search
USPC .................................................... 623/24–26
See application file for complete search history.

(56) References Cited

U.S. PATENT DOCUMENTS

| | | | | |
|---|---|---|---|---|
| 2009/0265018 | A1 | 10/2009 | Goldfarb et al. | |
| 2013/0006159 | A1* | 1/2013 | Nakashima | A61H 1/024 602/23 |
| 2013/0310949 | A1* | 11/2013 | Goldfarb | A61F 2/68 623/27 |
| 2015/0297364 | A1* | 10/2015 | Goldfarb | A61F 2/66 623/47 |
| 2016/0206447 | A1* | 7/2016 | Auberger | A61F 2/64 |

OTHER PUBLICATIONS

Andersson, GBJ et al. "Correlations between changes in gait and in clinical status after knee arthroplasty." Acta Orthopaedica Scandinavica 52.5: 569-573; especially pp. 570-571 (Jul. 8, 2009) (Year: 2009).*

Gregg, R.D. "Towards Biometric Virtual Constraint Control of a Powered Prosthetic Leg" IEEE Transactions on Control Systems Technology vol. 22, No. 1, pp. 246-254, especially 246 (Jan. 2014) (Year: 2014).*

Gregg et al.; Gregg, Robert D., et al. "Virtual constraint control of a powered prosthetic leg: From simulation to experiments with transfemoral amputees." Robotics, IEEE transactions on 30.6: 1455-1471; especially pp. 2-5, 8, 10, 16-18, 21 (Dec. 13, 2014).

Mace, M et al. "A heterogeneous framework for real:time decoding of bioacoustic signals: Applications to assistive interfaces and prosthesis control." Expert Systems with Applications 40.13: 5049-5060; especially p. 5054 (Mar. 28, 2013).

Andersson, GBJ et al. "Correlations between changes in gait and in clinical status after knee arthroplasty." Acta Orthopaedica Scandinavica 52.5: 569-573; especially pp. 570-571 (Jul. 8, 2009).

International Search Report and Written Opinion in International Application No. PCT/US16/17453, dated May 4, 2016.

* cited by examiner

SYSTEMS AND METHODS FOR PROSTHETIC DEVICE CONTROL

CROSS-REFERENCE TO RELATED APPLICATION

This application is a national phase application under 35 U.S.C. § 371 of International Application No. PCT/US2016/017453, filed Feb. 11, 2016, which claims priority to U.S. Provisional Patent Application Ser. No. 62/115,350 filed Feb. 12, 2015, the contents of which are incorporated by reference herein.

GOVERNMENT LICENSE RIGHTS

This invention was made with government support under DP2HD080349 by the National Institute of Child Health and Human Development of the NIH. The government has certain rights in the invention.

BACKGROUND INFORMATION

In the field of prosthetics and orthotics (P&O) prosthetic devices exist that allow increased mobility for amputees or other individuals without a lower limb (herein referred to generally as "amputees"). Orthotic devices can allow increased mobility for individuals who have suffered a stroke, a spinal cord injury, or other condition impairing the lower limbs, or who suffer a disease, such as peripheral neuropathy, that limits the full use of one or more lower limbs.

Some prosthetic devices are passive, requiring amputees to expend far more energy performing tasks, such as standing, walking, running, or climbing stairs, than a fully-limbed individual would otherwise expend. Other prosthetic devices are powered, offering amputees the promise of regaining the ability to perform all tasks that a sound-limbed individual can perform, including standing, walking, running, and climbing stairs. A powered prosthetic device uses motors to apply torques to one or more joints in the limb, causing the joint to flex or stiffen with applied levels of power and therefore assisting a user's movement during a task. The pattern of motion repeating from step to step during a task or other locomotion is called a "gait." A gait may be divided into a "stance" phase, wherein the foot of the leg is in contact with the ground, and a "swing" phase, wherein the foot of the leg is not in contact with the ground. The stance phase and the swing phase each may be divided into more discrete phases; for instance, swing phase may be divided into early swing phase (knee flexion) and late swing phase (knee extension).

Powered prosthetic devices include a microprocessor that is programmed with a control system for the control of the device. Control systems known in the art for powered prosthetic devices rely on various strategies. One control system relies on information from sensors coupled to the lower limb device, which provide real-time information about the present joint angles, velocities, and torques when the device is in operation. The control system compares information received from sensors to a look-up table of desired joint angles, velocities, or torques over time. One disadvantage of this system is that it is not adaptable to varying tasks or conditions. The look-up table is based on a gait cycle that has been divided into multiple time periods, each termed "phases," that have observable behaviors. An example of a "phase" is when the ankle pushes off at the end of a step cycle, as shown in FIG. 1. In the prior art, a prosthetic leg sequentially mimics human behavior by implementing a different control model for each discrete phase of gait. FIG. 1 further shows how the velocity, angle, or torque depend on a time variable set in each phase of the gait cycle, in the prior art. This prior art approach requires each controller to be manually tuned and is not robust to external perturbations that push joint kinematics (i.e., angles and velocities) forward or backward in the gait cycle, which cause the wrong controller to be used.

Prior art systems that rely on segmentation of the gait cycle employ a variety of control strategies, which may enforce different reference trajectories, joint impedances (the "impedance" of a joint being a measurement of its stiffness/viscosity), and/or reflex models, based on discrete phases of the gait cycle. Such control systems are disclosed in the following articles, which are incorporated by reference: F. Sup, A. Bohara, and M. Goldfarb, "Design and control of a powered transfemoral prosthesis," Int J Rob Res, vol. 27, pp. 263-273, Feb. 1, 2008; F. Sup, H. A. Varol, and M. Goldfarb, "Upslope walking with a powered knee and ankle prosthesis: initial results with an amputee subject," IEEE transactions on neural systems and rehabilitation engineering, vol. 19, pp. 71-8, February 2011; M. F. Eilenberg, H. Geyer, and H. Herr, "Control of a powered ankle-foot prosthesis based on a neuromuscular model," IEEE Transactions on Neural Systems and Rehabilitation Engineering, vol. 18, pp. 164-73, April 2010; and K. A. Shorter, G. F. Kogler, E. Loth, W. K. Durfee, and E. T. Hsiao-Wecksler, "A portable powered ankle-foot orthosis for rehabilitation," J Rehabil Res Dev, vol. 48, pp. 459-72, 2011.

One disadvantage of these control systems is that a highly-trained clinician must spend significant amounts of time to finely tune multiple control parameters for each individual user. These powered lower limb prostheses have many parameters that must be tuned for stance, including parameters relating to sequential impedance control, a joint muscle model, or lookup tables for tracking human data. Having multiple parameters that require precise tuning contributes substantially to the expense of a powered lower limb device.

SUMMARY

Exemplary embodiments of the present disclosure comprise a control strategy for a prosthetic device that unifies the entire gait cycle, eliminating the need to switch between controllers during different periods of an ambulatory gait. Existing control methods divide the gait cycle into several sequential periods with independent controllers, resulting in many patient-specific control parameters and switching rules that must be tuned by clinicians.

The use of a single controller can reduce the number of control parameters to be tuned for each patient, thereby reducing the clinical time and effort involved in fitting a powered prosthesis for a lower-limb amputee.

A significant aspect of unifying an entire gait cycle is the recognition that many ambulatory or locomotion functions (e.g. walking, running, climbing stairs, etc.) are performed in a repetitive manner so each of the angles used in the ambulatory function will repeat after a full gait cycle. Prior art systems and methods that break up the gait cycle into discrete phases eliminate the periodicity of the gait cycle because within each discrete phase there is not a periodic trajectory. Exemplary embodiments described herein embrace the fact that many ambulatory or locomotion functions are periodic. Accordingly, recognition of this periodic cycle provides for less complicated and more robust control designs.

Certain embodiments use a Discrete Fourier Transformation to design a single output function that acts as a virtual constraint and accurately characterizes the desired actuated joint motion over the entire gait cycle. The output function can be zeroed using feedback linearization to produce a single, unified controller. The virtual constraint is imposed on the prosthetic device through a control system as described herein. DFT allows one to encode a continuous periodic signal into a finite set of coefficients that accurately and completely describe the signal. In other embodiments, the unified virtual constraint may be created utilizing other techniques, including for example, a polynomial regression fit.

Exemplary embodiments include a method for controlling a prosthetic device, where the method comprises measuring a plurality of variables with one or more sensors, where the one or more sensors are operatively coupled to a controller, and where the controller is configured to control the prosthetic device comprising a plurality of joint elements. Exemplary embodiments may further include determining a value of a monotonic phasing variable based on measurements of the plurality of variables, and adjusting a joint element in response to the value of the monotonic phasing variable by enforcing a unified virtual constraint that controls an entire gait cycle of the prosthetic device.

In certain embodiments, the monotonic phasing variable. In specific embodiments, the monotonic phasing variable is a hip phase angle of a user of the prosthetic device. In particular embodiments, the monotonic phasing variable is a location of a center of mass of a user of the prosthetic device. In some embodiments, the entire gait cycle is an ambulatory cycle, and in specific embodiments, the ambulatory cycle is a walking cycle, a running cycle, and/or a stair climbing cycle.

In certain embodiments, the unified virtual constraint is created utilizing a Discrete Fourier Transform (DFT). In particular embodiments, the unified virtual constraint is created utilizing a polynomial regression fit. In some embodiments, the joint element comprises a knee joint, and in specific embodiments the joint element comprises an ankle joint. In certain embodiments, the joint element comprises a knee joint and an ankle joint.

In particular embodiments, the plurality of variables comprises an angle of a knee joint, a velocity of a knee joint, an angle of an ankle joint, and/or a velocity of an ankle joint. In certain embodiments, the entire gait cycle comprises a stance phase and a swing phase. In some embodiments, different control parameters are used for the stance phase and the swing phase to enforce the unified virtual constraint for the entire gait cycle of the prosthetic device.

Exemplary embodiments include a control system comprising: a plurality of sensors configured to measure a plurality of variables relating to a prosthetic device, and a controller operatively coupled to the plurality of sensors, where the controller is configured to determine a value of a monotonic phasing variable based on measurements of the plurality of variables and where the controller is configured to adjust a joint element of the prosthetic device in response to the value of the monotonic phasing variable by enforcing a unified virtual constraint that controls an entire gait cycle of the prosthetic device.

In certain embodiments, the monotonic phasing variable is a hip position of a user of the prosthetic device. In specific embodiments, the monotonic phasing variable is a hip phase angle of a user of the prosthetic device. In particular embodiments, the monotonic phasing variable is a location of a center of mass of a user of the prosthetic device. In some embodiments, the entire gait cycle is an ambulatory cycle. In particular embodiments, the ambulatory cycle is a walking cycle, a running cycle, and/or a stair climbing cycle.

In some embodiments, the unified virtual constraint is created utilizing a Discrete Fourier Transform (DFT). In specific embodiments, the unified virtual constraint is created utilizing a polynomial regression fit. In some embodiments, the joint element comprises a knee joint, and in specific embodiments the joint element comprises an ankle joint. In certain embodiments, the joint element comprises a knee joint and an ankle joint.

In particular embodiments, the plurality of variables comprises an angle of a knee joint, a velocity of a knee joint, an angle of an ankle joint, and/or a velocity of an ankle joint. In certain embodiments, the entire gait cycle comprises a stance phase and a swing phase. In some embodiments, different control parameters are used for the stance phase and the swing phase to enforce the unified virtual constraint for the entire gait cycle of the prosthetic device.

Exemplary embodiments include a prosthetic device comprising: a plurality of sensors configured to measure a plurality of variables relating to the prosthetic device; and a controller operatively coupled to the plurality of sensors, where the controller is configured to determine a value of a monotonic phasing variable based on measurements of the plurality of variables and where the controller is configured to adjust a joint element of the prosthetic device in response to the value of the monotonic phasing variable by enforcing a unified virtual constraint that controls an entire gait cycle of the prosthetic device.

In certain embodiments, the monotonic phasing variable is a hip position of a user of the prosthetic device. In specific embodiments, the monotonic phasing variable is a hip phase angle of a user of the prosthetic device. In particular embodiments, the monotonic phasing variable is a location of a center of mass of a user of the prosthetic device. In some embodiments, the entire gait cycle is an ambulatory cycle. In particular embodiments, the ambulatory cycle is a walking cycle, a running cycle, and/or a stair climbing cycle.

In some embodiments, the unified virtual constraint is created utilizing a Discrete Fourier Transform (DFT). In specific embodiments, the unified virtual constraint is created utilizing a polynomial regression fit. In some embodiments, the joint element comprises a knee joint, and in specific embodiments the joint element comprises an ankle joint. In certain embodiments, the joint element comprises a knee joint and an ankle joint.

In particular embodiments, the plurality of variables comprises an angle of a knee joint, a velocity of a knee joint, an angle of an ankle joint, and/or a velocity of an ankle joint. In certain embodiments, the entire gait cycle comprises a stance phase and a swing phase. In some embodiments, different control parameters are used for the stance phase and the swing phase to enforce the unified virtual constraint for the entire gait cycle of the prosthetic device.

In the present disclosure, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

DETAILED DESCRIPTION OF ILLUSTRATIVE EMBODIMENTS

Although defined in a similar manner to physical/contact constraints, virtual constraints are enforced by actuator torques rather than external physical forces. The vast majority of virtual constraints used in bipedal robots are holonomic, [13], [23], [32], [12], [33]; therefore, one can translate these design principles into a prosthetic framework by considering virtual holonomic constraints:

$$h(q)=0 \tag{Eq. A}$$

where q is the vector of generalized coordinates (i.e., all joint angles) of the system, and h is a vector-valued function defining one virtual constraint per actuated degree-of-freedom (DOF), e.g., the knee and ankle of the prosthesis. Eq. A is called a unified virtual constraint if it can be used to control the actuated joints through a complete gait cycle (i.e., one stride) without changes to the function h.

Meaningful virtual constraints, i.e., output functions h(q), can be defined in a variety of ways. Reviewing previous work in bipedal robotics (e.g., [23], [13], [12]), virtual constraints can be used to control the actuated joints specified by $h_o(q)=(\theta_a, \theta_k)^T$ to a desired (vector-valued) trajectory $h_d(\Theta(q))$ as a function of a monotonic quantity $\Theta(q)$. This quantity, known as the phase variable or timing variable, provides a unique representation of the gait cycle phase to drive forward the desired pattern in a time-invariant manner. In this case, the output function of (Eq. A) would be defined by $h(q)=h_o(q)-h_d(\Theta(q))$. In the prior art the desired pattern h $_d$ is often defined first as a function of time (via boundary-constrained optimization) and then reparameterized into a function of $\Theta(q)$ [23].

Given desired virtual constraints (Eq. A), the goal of a virtual constraint controller is to drive output function h(q) to zero using actuator torques. Therefore, the control system output $$y:=h(q) \tag{Eq. B}$$

corresponds to tracking error from the desired constraint (Eq. A).

Some torque control methods are better suited than others at driving this output to zero. If one does not start with a desired joint pattern ha (see discussion above), it is not always possible to solve a virtual constraint (Eq. A) for a unique joint trajectory as needed for joint impedance methods [4], [7], [9], [34]. Bipedal robots typically enforce virtual constraints using partial (i.e., input-output) feedback linearization [23], which has appealing theoretical properties including exponential convergence [11], reduced-order stability analysis [23], and robustness to model errors [13]. However, the application of this method to prosthetics presents unique challenges with human-machine interaction.

Figure 1:
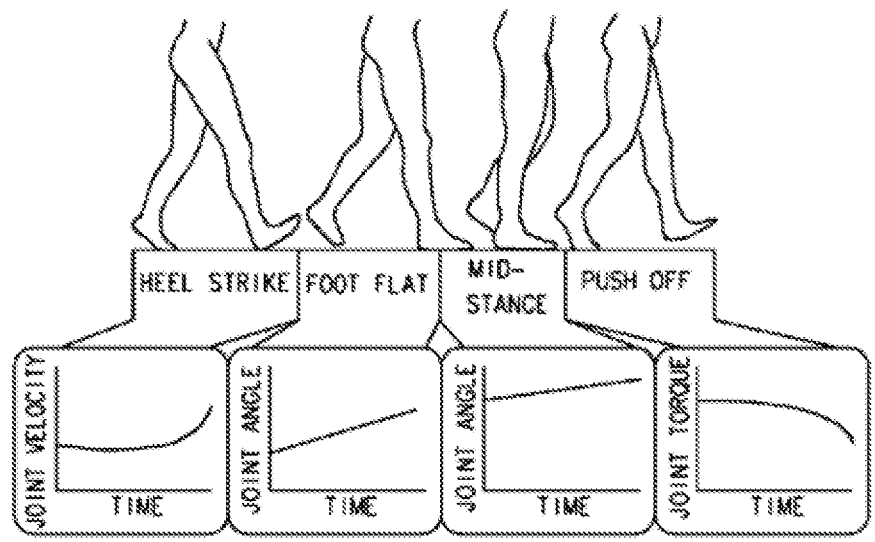
FIG. 1 illustrates a schematic view of gait phases used in the prior art to control lower prosthetic limb devices.
Figure 2:
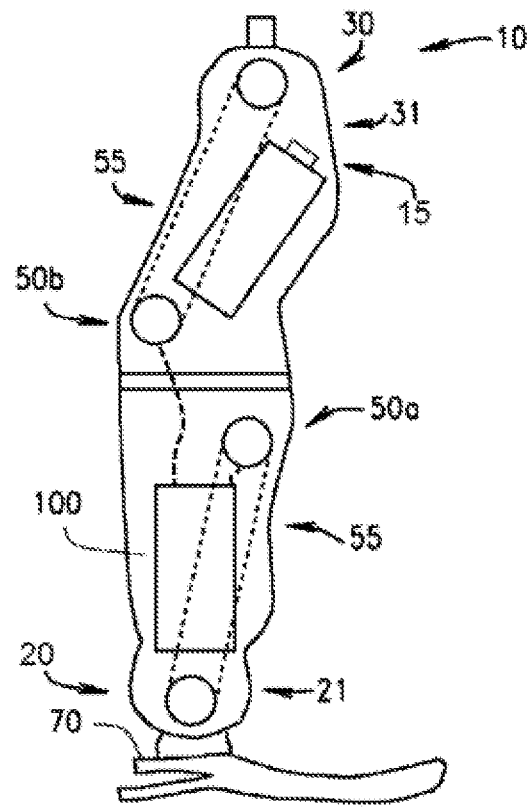
FIG. 2 illustrates a schematic of a prosthetic device programmed with the control strategies according to exemplary embodiments.

FIG. 2 discloses a prosthetic limb 10 that may be programmed according to the exemplary embodiments of control methods described herein. In the embodiment shown, limb 10 comprises a powered ankle 21 and powered knee 31. Each joint can be coupled to an encoder (not shown) that can measure the angle and velocity of the joint. In addition, each joint is coupled to a motor 50 and optionally a transmission 55 that together are capable of producing physiological levels of torque. 50$a$ indicates the motor coupled to the ankle and 50$b$ indicates the motor coupled to the knee. In certain embodiments, e.g. for a user weighing up to 90 kg, at least 80 Nm of torque may be utilized. In particular embodiments, limb 10 and its related components may be the prosthetic limb with powered knee and ankle joints developed by the Vanderbilt Center for Intelligent Mechatronics (Vanderbilt University, TN) and commercialized by Freedom Innovations (Irvine, Calif.) or another powered prosthetic limb. Limb 10 and its components can be powered by a battery 15 in specific embodiments.

One embodiment of the torque control method for a virtual constraint is impedance control (which is equivalent to proportional-derivative control in this context). In such an embodiment, the virtual constraint output would be changing Theta continuously. In the embodiment shown, limb 10 includes controller 100 that is programmed to run two control loops, a joint-level control loop 301 and a motor-level control loop 302 (shown in FIG. 3). In certain embodiments, controller 100 can have an update rate of at least 500 Hz or 1 kHz or more. If controller 100 accepts only impedance commands (i.e. stiffness Kp, viscosity Kd, and equilibrium angle Theta), its impedance controller can be replaced by a desired virtual constraint controller. This can be done for each joint by sending the controller 100 any standard Kp and Kd values and an equilibrium angle given by Theta=JointAngle+(Kd*Joint_Velocity+Torque_Desired)/Kp, where Torque_Desired is the torque calculated from sensor measurements by a torque controller, including for example, one of the torque controllers described herein. In exemplary embodiments, the joint-level loop 301 calculates and re-sends the equilibrium angle for each joint at the same or a different frequency at which the motor-level loop 302 operates.

Figure 3:
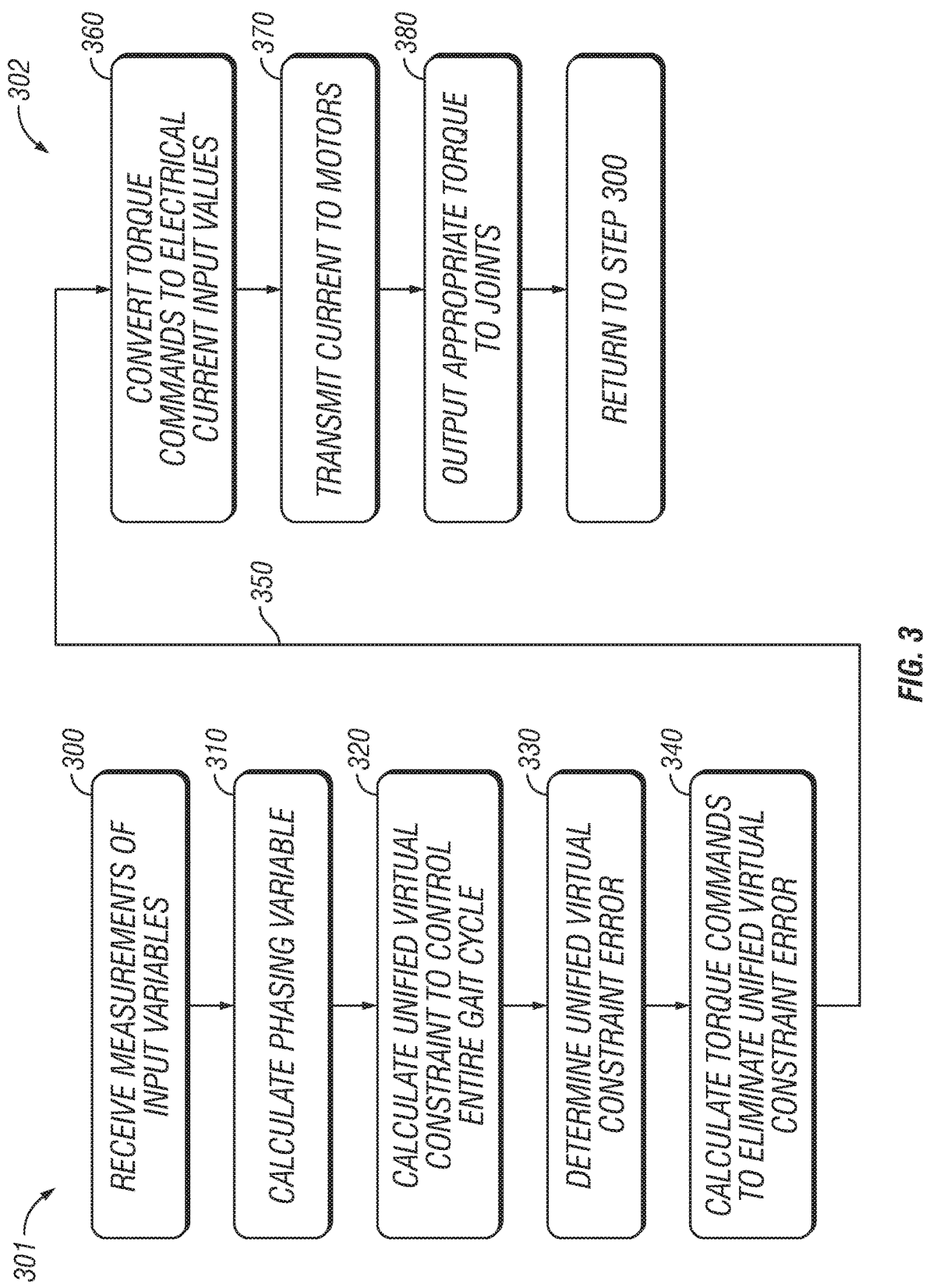
FIG. 3 illustrates a control strategy flow chart for the operation of the prosthetic device of FIG. 2.

Controller 100 can be programmed with a control strategy for the control of prosthetic device 10. FIG. 3 discloses a flow chart for the operation of prosthetic device 10 during operation. In 300, joint-level control loop 301 receives measurements of one or more variables relating to elements of prosthetic device 10. In 310 and 320, joint-level control loop 301 calculates a value of a phasing variable and unified virtual constraint to control the entire gait cycle. Joint-level control loop 301 determines the unified virtual constraint error in step 330, and in step 340 calculates torque commands to eliminate the unified virtual constraint error. In step 350, joint-level control loop 301 transmits the torque commands to motor-level control loop 302. In step 360, motor-level control loop 302 then converts the torque commands to electrical current input values that indicate the amount of current to be applied to motors 50. In step 370, control loop 302 causes current to flow to motors 50 on the basis of the current input values. In certain embodiments utilizing closed-loop control, ammeters 45 can measure the current flowing to motors 50 and current flow may be corrected to the desired level if needed. In step 380 motors 50 and transmissions 55 output the appropriate torques to ankle joint 21 and knee joint 31. In particular embodiments, again utilizing closed-loop control, strain gages 35 may measure torques at ankle 21 and knee 31 and current flow may be corrected to achieve intended torque control. Controller 100 may then return to step 300.

In one embodiment, controller 100 may comprise two microcontrollers, including one that implements motor-level control loop 302 and one microcontroller that implements joint-level control loop 301. The PIC32 (Microchip Technologies Inc., Chandler, Ariz.) or a similar microcontroller or a digital signal processor may be used for each microcontroller. The microcontrollers may communicate over the CAN protocol or another digital medium or an analog medium. The motor-level controller can accept torque commands to drive motors 50. Alternately, the motor-level controller may accept impedances instead of torque commands, in which case an additional impedance inversion stage is needed in the joint-level control loop 301. In certain embodiments, controller 100 may comprise a single microcontroller.

As previously mentioned, the unified virtual constraint may also be created utilizing various techniques. In certain embodiments, the unified virtual constraint may be created utilizing a DFT. In other embodiments, the unified virtual constraint may be created utilizing other techniques, including for example, a polynomial regression fit.

In exemplary embodiments the unified virtual constraint error may be calculated in one of various manners. In certain exemplary embodiments, the unified virtual constraint error may be calculated utilizing proportional derivative control. In other embodiments, the unified virtual constraint error may be calculated utilizing feedback linearization.

In exemplary embodiments, the phasing variable may be, for example, the position of the center of mass or the hip position for a person utilizing prosthetic device 10. Any variable that can be measured or calculated and is monotonic throughout the entire gait cycle during a steady gait may be used as the phasing variable.

Figure 4:
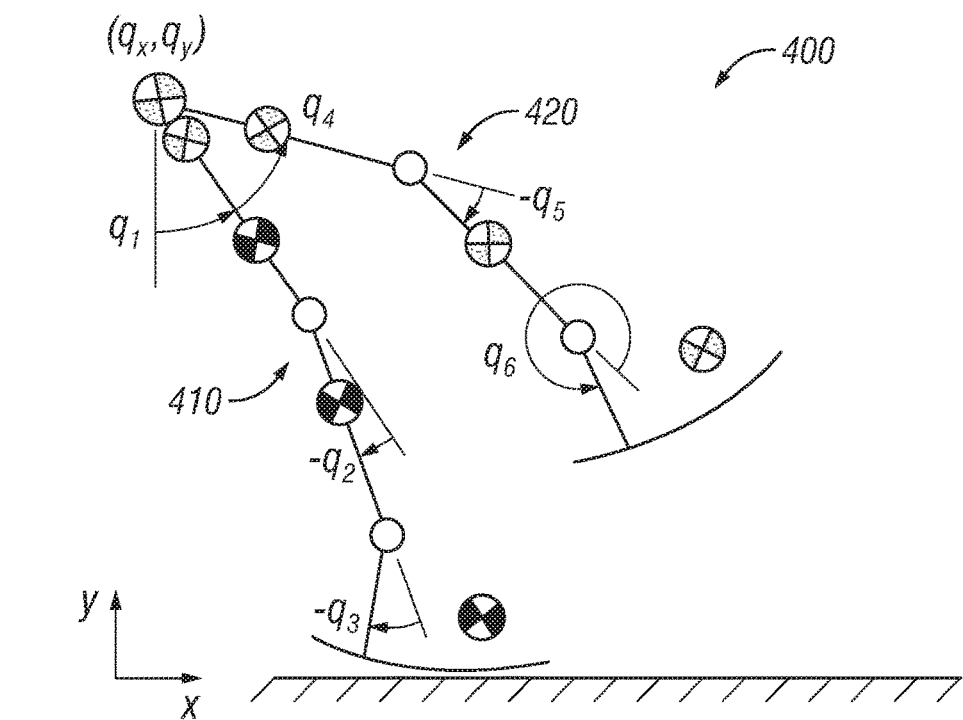
FIG. 4 illustrates a schematic of the unilateral, transfemoral amputee model.

Referring now to FIG. 4, a schematic of a unilateral, transfemoral amputee model 400 is shown comprising a prosthetic device 410 and a human leg 420. The generalized coordinates used in model 400 are indicated with q terms. In the model shown, angle $q_1$ is unactuated and for modeling purposes, angles $q_{2-6}$ have ideal actuators.

Model 400 shown in FIG. 4 comprises seven leg segments plus a point mass at the hip to represent the upper body [18] and serve as the phasing variable. Calculation of the hip position is described in further detail herein, and the control systems described herein may use hip position as a phase variable for those tasks where hip position is monotonic during the entire gait cycle, including walking on a level surface, walking uphill, walking downhill, heel-to-toe running, or stair climbing.

The full model shown in FIG. 4 is divided into a prosthesis subsystem comprising a prosthetic thigh, shank, and foot, and a human subsystem comprising a contralateral thigh, shank, and foot, a residual thigh on the amputated side, and a point mass at the hip. For modeling purposes, it is assumed that the prosthetic thigh and residual stump are rigidly attached. The thigh and shank segments are modeled using rigid links with both mass and inertia. Rather than model all of the degrees of freedom of the foot, the function of the foot and ankle is modeled using a circular foot [19], [20] plus an ankle joint to capture the stance ankle's positive work [21].

For the purpose of simulating the full model, each stride (a complete gait cycle) can be modeled using four distinct periods. For simulation, a stride starts just after the transition from contralateral stance to prosthesis stance and proceeds through the prosthesis stance period, an impact event, the contralateral stance period and a second impact. The two stance periods can be modeled with continuous, second-order differential equations, and the two impact periods can be modeled using an algebraic mapping that relates the state of the biped at the instant before impact to the state of the biped at the instant after impact.

In this simulation method, the equations of motion during the single support period for a subsystem can be found using the method of Lagrange [18], [22] and written as:

$$M_{ij}\ddot{q}_i + C_{ij}\dot{q}_i + N_{ij} = B_{ij}u_i + J_{ij}^T F. \quad (1)$$

The subscript i indicates which subsystem the term is for, with P indicating the prosthesis subsystem and H indicating the human subsystem. The subscript j indicates which leg is in stance, with P indicating that the prosthesis is in stance and C indicating that the contralateral leg is in stance (and that the prosthesis is in swing). Because the biped is assumed to roll without slip, the absolute angle is unactuated. The ideal actuators at the remaining joints generate torque $u_i$. The interaction forces between the human and prosthesis at the socket are given by F and depend on the motion of both subsystems. Eq. 1 can also be written as a first-order system:

$$\dot{x}_i = f_{ij}(x_i) + g_{ij}(x_i)u_i + p_{ij}(x_i)F, \quad (2)$$

where $$x_i = \begin{bmatrix} q_i \\ \dot{q}_i \end{bmatrix},$$

$$f_{ij}(x) = \begin{bmatrix} \dot{q}_i \\ -M_{ij}^{-1}(C_{ij}\dot{q}_i + N_{ij}) \end{bmatrix},$$

$$g_{ij}(x) = \begin{bmatrix} 0 \\ M_{ij}^{-1}B_{ij} \end{bmatrix},$$

$$p_{ij}(x) = \begin{bmatrix} 0 \\ M_{ij}^{-1}J_{ij}^T \end{bmatrix}.$$

The impacts can be modeled using equations of the form $$q_i^+ = q_i^-, \quad (3)$$

$$\dot{q}_i^+ = A_{ij}\dot{q}_i^- + A_{ij}\mathcal{F}, \quad (4)$$

where $\mathcal{F}$ is the socket interaction impulse and depends on the pre-impact state of both subsystems [18], the superscript '−' refers to the instant before impact, and the superscript '+' refers to the instant after impact.

Feedback Linearizing Control

To control both the prosthesis and the human, feedback linearization with virtual constraints is used [11], [23], although the prosthesis controller does not depend on the form of the human controller. Note the human leg is controlled in this manner for purposes of simulation. To perform feedback linearization, the desired motion of the actuated variables is encoded in output functions to be zeroed [23]. These output functions are the virtual constraints:

$$y_{ij} = h_{ij}(q_i) = H_{0i}q_i - h_{ij}^d(\theta_i(q_i)), \quad (5)$$

where $h_{ij}$ is a vector-valued function to be zeroed, $H_{0i}$ is a matrix that maps the generalized coordinates to the actuated angles, $h_{ij}^d$ is a vector-valued function of the desired joint angles, and $\theta_i$ is the phase variable. For human leg 420, a separate output function is defined for the prosthesis single support period and for the contralateral single support period, and $h_{Hj}^d$ is encoded using polynomials. For prosthetic device 410, a single, unified output function $h_P$ is defined for the entire stride, i.e., both the stance and swing periods of the prosthesis. Note that $h_{ij}$ and $h_{ij}^d$ are functions of configuration only since the motion is parametrized using a kinematic phase variable and not by time explicitly. Differentiating Eq. 5 twice and substituting in the equations of motion (Eq. 2) for $\ddot{q}_i$ gives the output dynamics [16]

$$\ddot{y}_{ij} = L_{f_{ij}}^2 h_{ij} + L_{g_{ij}}L_{f_{ij}}h_{ij} \cdot u_i + L_{p_{ij}}L_{f_{ij}}h_{ij} \cdot F, \quad (6)$$

where standard Lie derivative notation [11] has been used and the terms are given by $$L_{f_{ij}}^2 h_{ij} = \frac{\partial}{\partial q_i}\left(\frac{\partial h_{ij}}{\partial q_i}\dot{q}_i\right)\dot{q}_i - \frac{\partial h_{ij}}{\partial q_i}M_{ij}^{-1}(C_{ij}\dot{q}_i + N_{ij}),$$

$$L_{g_{ij}}L_{f_{ij}}h_{ij} = \frac{\partial h_{ij}}{\partial q_i}M_{ij}^{-1}B_{ij},$$

$$L_{p_{ij}}L_{f_{ij}}h_{ij} = \frac{\partial h_{ij}}{\partial q_i}M_{ij}^{-1}J_{ij}^T.$$

To cancel the nonlinearities in the output dynamics, set $\ddot{y}_{ij} = v_{ij}$ and solve for the input torques:

$$u_i = \alpha_{ij} + \beta_{ij} \cdot F, \quad (7)$$

where $v_{ij}$ is a stabilizing controller, F is known through measurement, and $$\alpha_{ij} = L_{g_{ij}}L_{f_{ij}}h_{ij}^{-1}(v_{ij} - L_{f_{ij}}^2 h_{ij}),$$

$$\beta_{ij} = -L_{g_{ij}}L_{f_{ij}}h_{ij}^{-1} \cdot L_{p_{ij}}L_{f_{ij}}h_{ij}.$$

Virtual Constraint Design by DFT

In this embodiment, the objective is to create output functions of virtual constraints that characterize the desired knee and ankle motion over the entire stride of prosthetic device 410. The output function is time-invariant and depends on a phase variable that is strictly monotonic and unactuated [23]. As previously stated, for this embodiment, the phase variable was chosen as the hip x-position $q_x$, which is measured relative to a coordinate frame created at the impact transition from the contralateral stance to the prosthesis stance period. This phase variable monotonically increases for one complete gait stride, which allows one output function to represent one joint's motion over the entire stride. Taking advantage of the periodic kinematics observed in human gait [24], the method of DFT can be used to parameterize the desired output function.

DFT is a linear transformation of a signal through a sequence of complex numbers to describe discrete frequency components of the signal. In general, the DFT representation is $$X[k] = \sum_{n=0}^{N-1} x[n]W_N^{kn}, k = 0, 1, \ldots, K \quad (8)$$

where N is the finite number of samples, K is the highest index for the finite sequence of k=0, 1, . . . N−1, and $W_N = e^{-j(2\pi/N)}$ is the complex quantity [25]. The original discrete signal in time domain is x[n], which is transformed to a discrete sequence in the frequency domain as X[k]. Because the signal is periodic, there are a finite number of discrete frequencies. As a result, Eq. 8 can be decomposed using a summation of sinusoids. To do so, Euler's relationship $e^{\pm j\Omega} = \cos\Omega \pm j\sin\Omega$, $\Omega \in \mathbb{R}$ can be used for $W_N$ within the DFT.

Obtaining the frequency content terms X[k] from a signal, the original signal can be reconstructed using Fourier Interpolation, where the basis function is given by:

$$x[n] = \frac{1}{N}\sum_{k=0}^{N-1} X[k]W_N^{-kn}, n \in \mathbb{N}_0 \quad (9)$$

and from n=0, 1, . . . , N−1.

Note that both x[n] and X[k] may be complex. Defining $X[k]=\text{Re}\{X[k]\}+j\,\text{Im}\{X[k]\}$ and $W_N^{-kn}=\text{Re}\{W_N^{-kn}\}+j\,\text{Im}\{W_N^{-kn}\}$, x[n] can be split into its real and imaginary parts:

$$\begin{aligned}x[n] &= \frac{1}{N}\sum_{k=0}^{N-1} (\text{Re}\{X[k]\} + j\text{Im}\{X[k]\}) \times \\ &\quad (\text{Re}\{W_N^{-kn}\} + j\text{Im}\{W_N^{-kn}\}) \\ &= \frac{1}{N}\sum_{k=0}^{N-1}(\text{Re}\{X[k]\}\text{Re}\{W_N^{-kn}\} - \text{Im}\{X[k]\}\text{Im}\{W_N^{-kn}\}) + \\ &\quad j(\text{Re}\{X[k]\}\text{Im}\{W_N^{-kn}\} + \text{Im}\{X[k]\}\text{Re}\{W_N^{-kn}\})\end{aligned} \quad (10)$$

For the virtual constraint design, the only portion necessary for the Fourier Interpolation equation x[n] is the real part. It can be validated from the calculated DFT signal that $X^*[k]=X[-k]$ and $X^*[N-k]=X[k]$ holds, which means that the imaginary components of Eq. 10 are zero [26]. The real, conjugate symmetric properties means the magnitude of X[k] for the $k^{th}$ index is the same for the $(N-k)^{th}$ index [27]. Also, it is clear that the gait kinematic signal is a real-valued sequence. Therefore, if the signal meets the real, conjugate symmetric properties above then this simplifies Eq. 10 to:

$$x[n] = \frac{1}{N}\sum_{k=0}^{N-1} \text{Re}\{X[k]\}\text{Re}\{W_N^{-kn}\} - \text{Im}\{X[k]\}\text{Im}\{W_N^{-kn}\} \quad (11)$$

where the summation terms are only the real part of the Fourier Interpolation. This can be represented by a function with a set of frequency terms from 0 up to N/2, the Nyquist sampling frequency, which is half the number of N samples in the discrete, equally spaced signal. Recall the magnitudes of X[k] and X[N−k] are equal due to the signal being a real-valued sequence, so the interpolation only needs to be computed for half the amount of N samples, as beyond N/2+1 the samples are duplicate values for the DFT. This results in the following exact representation of the original signal $$x[n] = \frac{1}{2}\alpha_0 + \sum_{k=1}^{\frac{N}{2}-1}[\alpha_k\text{Re}\{W_N^{-kn}\} - \beta_k\text{Im}\{W_N^{-kn}\}] + \frac{1}{2}\alpha_{\frac{N}{2}}\text{Re}\left\{W_N^{-\frac{N}{2}n}\right\}, \quad (12)$$

$$n = 0, 1, \ldots, N-1$$

where $\alpha_k=2\,\text{Re}\{X[k]\}\in\mathbb{R}$ and $\beta_k=2\,\text{Im}\{X[k]\}\in\mathbb{R}$ are the scalar coefficients [28]. Note that Eq. 12 is a lower order functional representation of Eq. 11.

The Fourier interpolation presented in Eq. 12 is used to create the unified desired output function, $h^d_P$, for the entire gait cycle. Because of the unified prostheses controller there is a single output function, $h_P$, used for both stance and swing period. This is in contrast to the human controller that requires four output functions $h_{HP}$ and $h_{HC}$. To do so, the desired angular trajectories of the knee and ankle are sampled over the entire gait cycle (e.g., from [21], [24], and [29]) at n discrete, equally-spaced values of the phase variable. The phase variable can be normalized using $$S_P(\theta_P(q_P)) = \frac{\theta_P - \theta_P^+}{\theta_P^- - \theta_P^+} \quad (13)$$

where the '+' signifies the start of the stance period for the prosthetic device 410 and the '−' indicates the end of its swing period. Using Eq. 8 to solve for X[k], the real and imaginary parts of X[k] are used to compute the coefficients of Eq. 12. Eq. 12 is used in the output function (Eq. 5) to generate the prosthesis virtual constraints:

$$h_P(q_P) = H_{0P}\cdot q_P - \quad (14)$$
$$\left(\frac{1}{2}\alpha_0 + \frac{1}{2}\alpha_{\frac{N}{2}}\cos(\pi N s_P) + \sum_{k=1}^{\frac{N}{2}-1}[\alpha_k\cos(2\pi k s_P) - \beta_k\sin(2\pi k s_P)]\right).$$

Simulation

Figure 5:
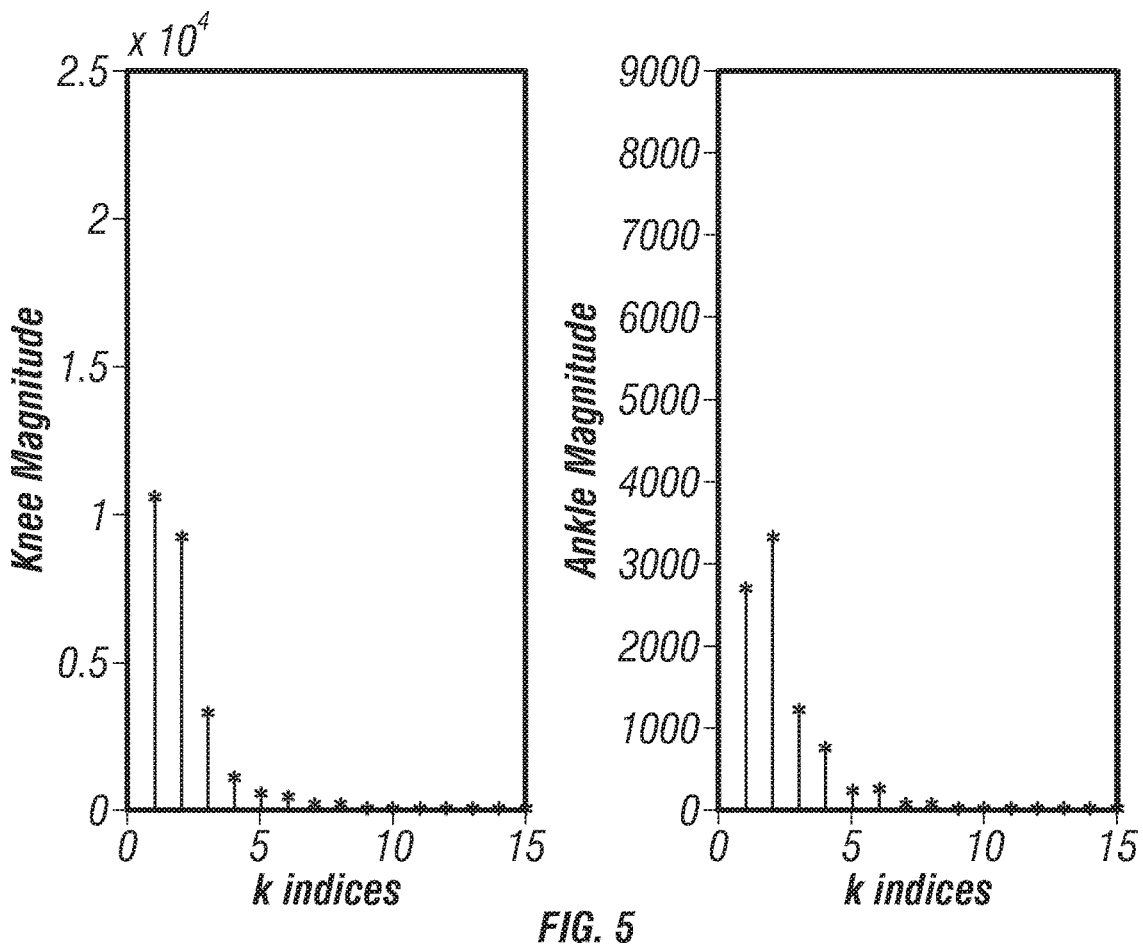
FIG. 5 illustrates a DFT plot for knee and ankle joint trajectories for the model of FIG. 4.

Using the method from the above section entitled Virtual Constraint Design by DFT, a unified output function for a prosthetic device 410 can be designed, comprising a knee and ankle joint as shown in FIG. 4. To begin, a desired trajectory that generates a stable gait is needed. For a prosthesis controller, it is generally desirable to mimic human able-bodied motion, so the desired trajectory can be chosen from one of many gait studies [24], [29]. For this simulation work, the trajectory was chosen based on a stable, HZD-based model designed to predict healthy human walking [18]. Using MATLAB to determine the DFT X[k] of the desired gait trajectory, the real and imaginary parts of X[k] and $W_N^{-kn}$ can be computed to create the Fourier Interpolation in Eq. 12. The DFT plot shown in FIG. 5 for the predetermined knee and ankle joint trajectories shows that between the $10^{th}$ and the Nyquist sampling frequency of N/2, the magnitude is approximately zero and will not have significant impact in recreating the joint trajectory for $h^d_P$. As a result, only the first 10 terms in Eq. 12 provide useful information for the Fourier Interpolation, so the series can be truncated to $k\in\{1,\ldots,10\}$. Therefore, the linear transformation for $h_i^d$ will have a minimal number of coefficients, which lessens the computational complexity of the feedback linearization around $y_q$.

Figure 6:
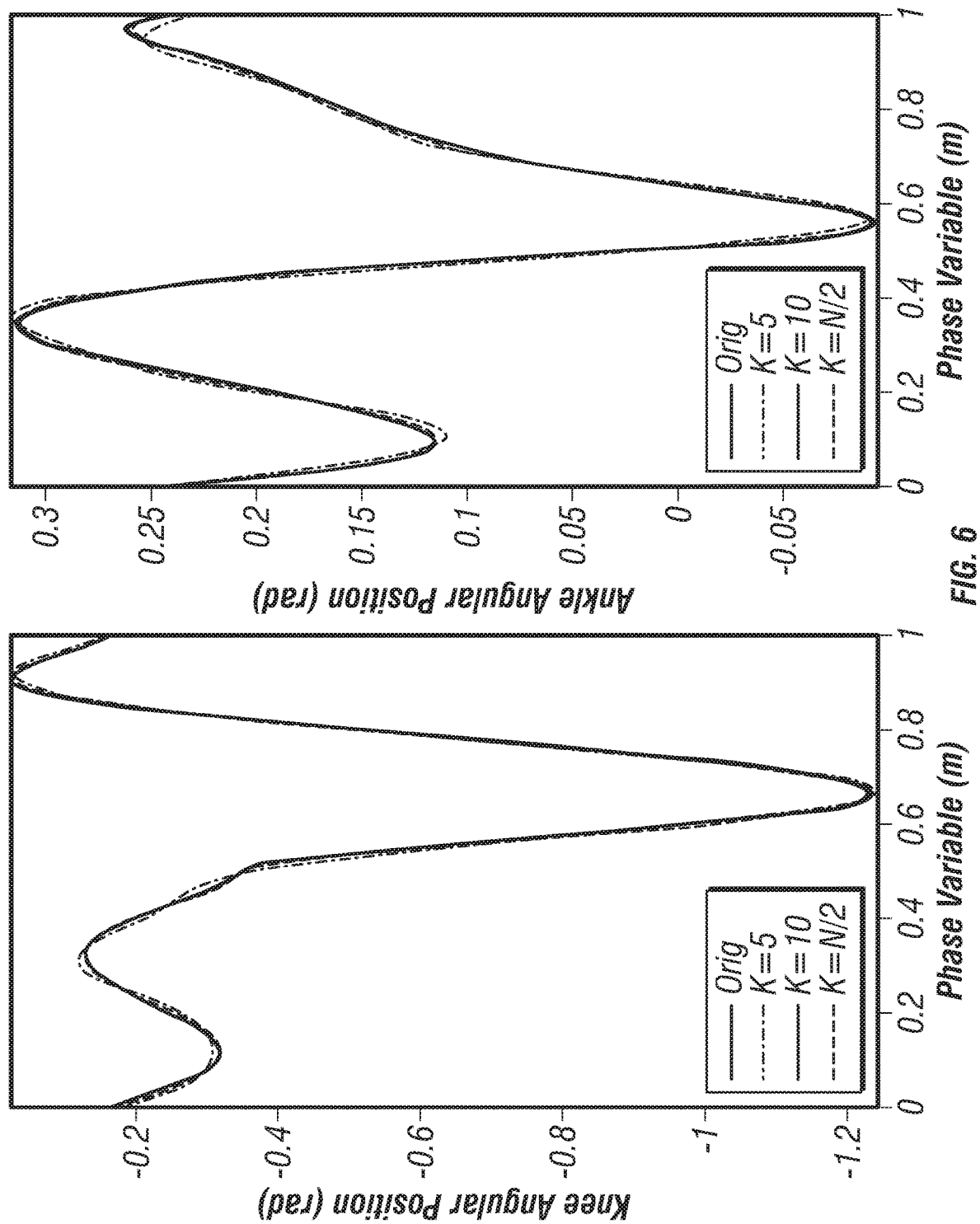
FIG. 6 illustrates graphs of prosthetic leg output functions for ankle and knee joint angle trajectories versus the normalized phase variable for the model of FIG. 4.

For each joint, desired output functions with K=5, 10 and N/2 were found, where K is the highest index for k in Eq. 14 (see FIG. 6). The lowest order function K=5 is an adequate representation of the original joint trajectory for both the ankle and knee with a coefficient of determination, r=0.995 and r=0.999, respectively. As expected, the output functions for K=10 and N/2 are almost identical, and match the desired trajectory better than K=5. The coefficient of determination for both functions at both joints is r=1.0.

Figure 7:
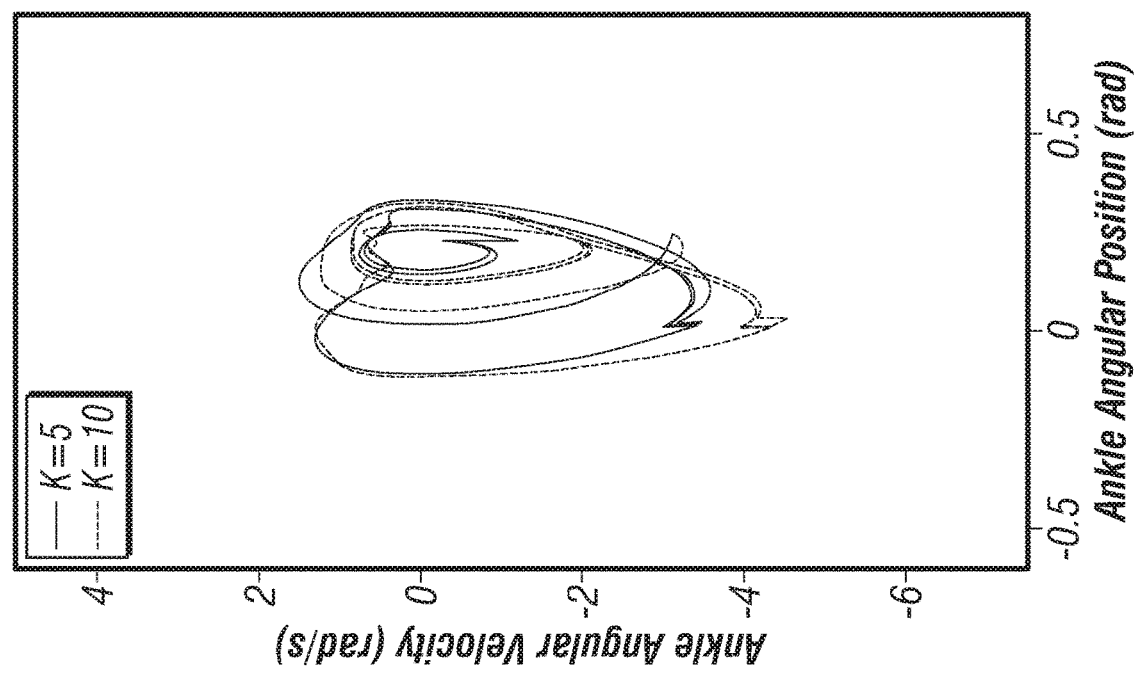
FIG. 7 illustrates graphs of angular phase portraits for prosthetic knee and ankle with K=5 and 10 for the output functions for the model of FIG. 4.
Figure 7:
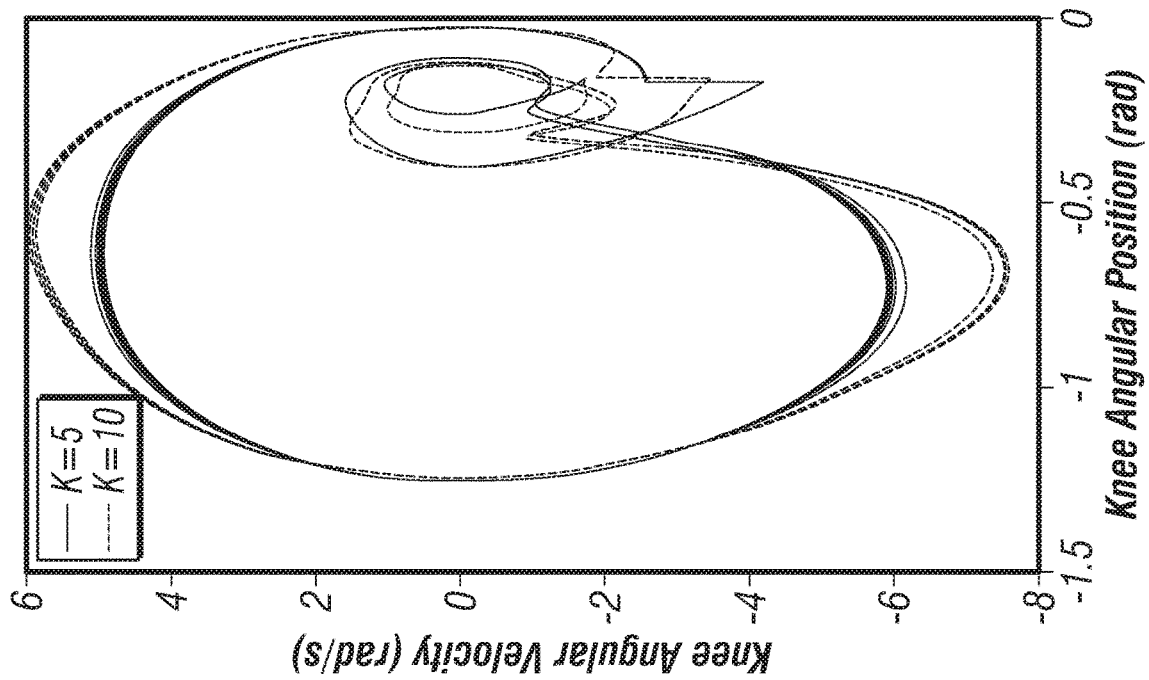
Figure 8:
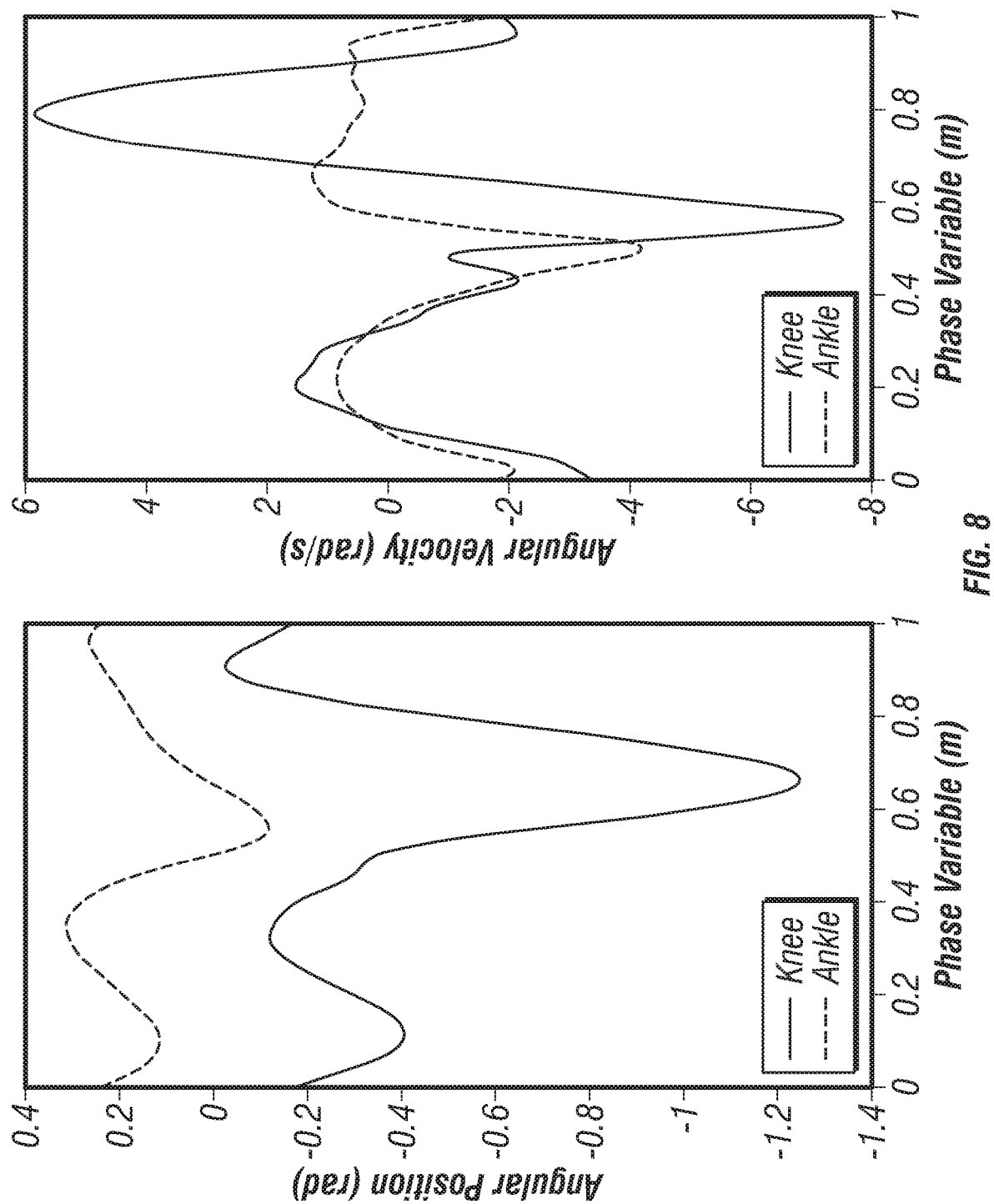
FIG. 8 illustrates graphs of simulated joint angles and velocities of prosthetic knee and ankle for the K=10 output function, plotted against the normalized phase variable for the model of FIG. 4.

The two lower-order output functions (K=5 and 10) were integrated into the amputee biped simulation as the virtual constraints for prosthetic device 410. For each set of output functions, the human leg 420 plus prosthetic device 410 was simulated until steady-state was reached (see FIG. 7). The two output functions converged to different periodic orbits due to the differences in the desired output functions. The steady-state prosthesis joint angles and velocities for K=10 are shown in FIG. 8. Given the faster convergence to a periodic orbit with K=10 (see FIG. 7) than the output function with K=5, the K=10 desired output function is preferred in this embodiment.

Experiments

Figure 9:
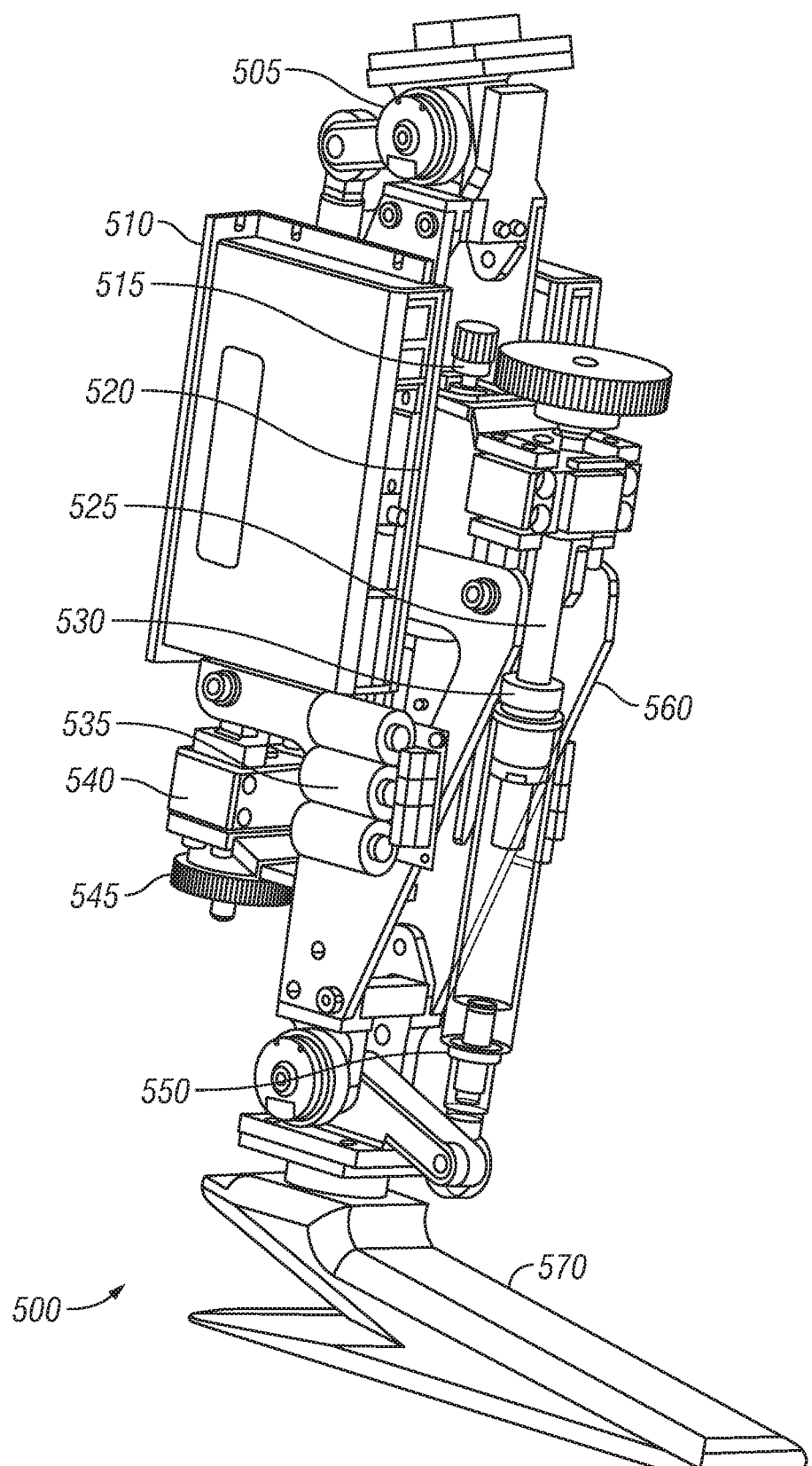
FIG. 9 illustrates a schematic of a prosthetic device programmed with the control strategies according to exemplary embodiments.

FIG. 9 also discloses a prosthetic limb 500 according to exemplary embodiments. This embodiment comprises a joint encoder 505, a motor amplifier 510, a first belt drive 515, a brushless direct current (BLDC) motor 520, a ball screw 525, and a ball nut 530. In addition, this embodiment comprises a motor filter card 535, a journal bearing 540, a second belt drive 545, and a load cell 550. Prosthetic limb 500 further comprises an upper support member 560 and a lower support member 570.

In the embodiment shown in FIG. 3, a linear ball screw actuator with a lever arm at the joint is utilized to satisfy the torque requirements, while limiting the overall weight of prosthetic limb 500. In the illustrated embodiment, the ball screw actuator is a duplicate design between both the knee and ankle actuation system for ease in overall design and manufacturing. In the embodiment shown, BLDC motor 520 is a high power-to-weight ratio BLDC motor, and in specific embodiments is a Maxon 200 Watt three phase BLDC Motor (Model: EC-4pole 30, Maxon Motor, Sachseln, Switzerland) weighing 300 grams. Such a configuration can provide the power to weight ratio needed to meet the actuator torque output at each joint.

For the knee actuator (with a 40 Nm torque requirement), a 2:1 timing belt drive can be used between the motor output and the ball screw. In the embodiment shown, the ankle actuator comprises a 4:1 timing belt drive. Sprockets utilized in prosthetic limb 500 can be machined from 7075 aluminum to reduce weight. In particular embodiments, the ball screw for both the knee and ankle can be a Nook 12 mm diameter, 2 mm lead ball screw (Model: PMBS 12x2r-3vw/0/T10/00/6K/184/0/S, Nook Industries, Cleveland, Ohio, USA). Such a configuration can convert the rotary motion from the motor with belt drive to linear motion of the ball nut driving the lever arm attached to the joint in generating torque output. The ball screw can be supported axially and radially by a double bearing support journal bearing (for example, model EZBK10-SLB, Nook Industries, Cleveland, Ohio, USA). To obtain the full range of motion at each joint with a linear actuator design, a motor mount can be used with a rotational pivot point to eliminate buckling of the ball screw and increase linear motion the ball screw can travel attached to the lever arm.

Figure 10:
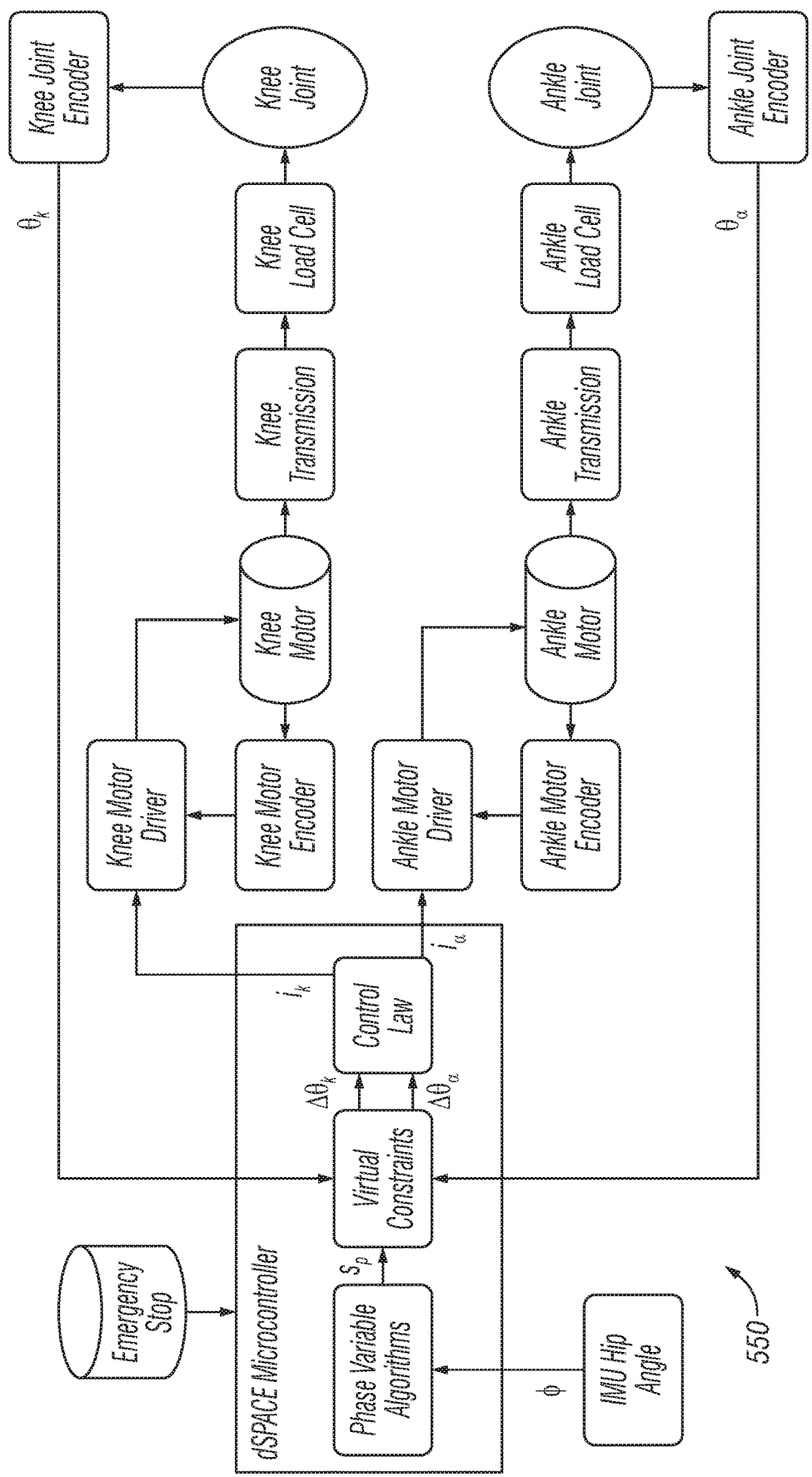
FIG. 10 illustrates a control system block diagram 550 for use with the embodiment of in FIG. 9.

FIG. 10 illustrates a control system block diagram 550 of the prosthetic limb 500 show in FIG. 9. In this embodiment, a dSPACE microcontroller contains the algorithms in computing the normalized phase variable sp from the IMU measuring hip angle φ as input to the virtual constraints. The virtual constraints produce knee error $\Delta\theta_k$ and ankle error $\Delta\theta_a$ to the control law in computing desired current commands for both the knee $i_k$ and ankle $i_a$. The desired current commands are sent to the motor drivers for handling the low-level current control loop to commutate the motors to drive the timing belt and ball screw transmission to actuate the joints.

Figure 11:
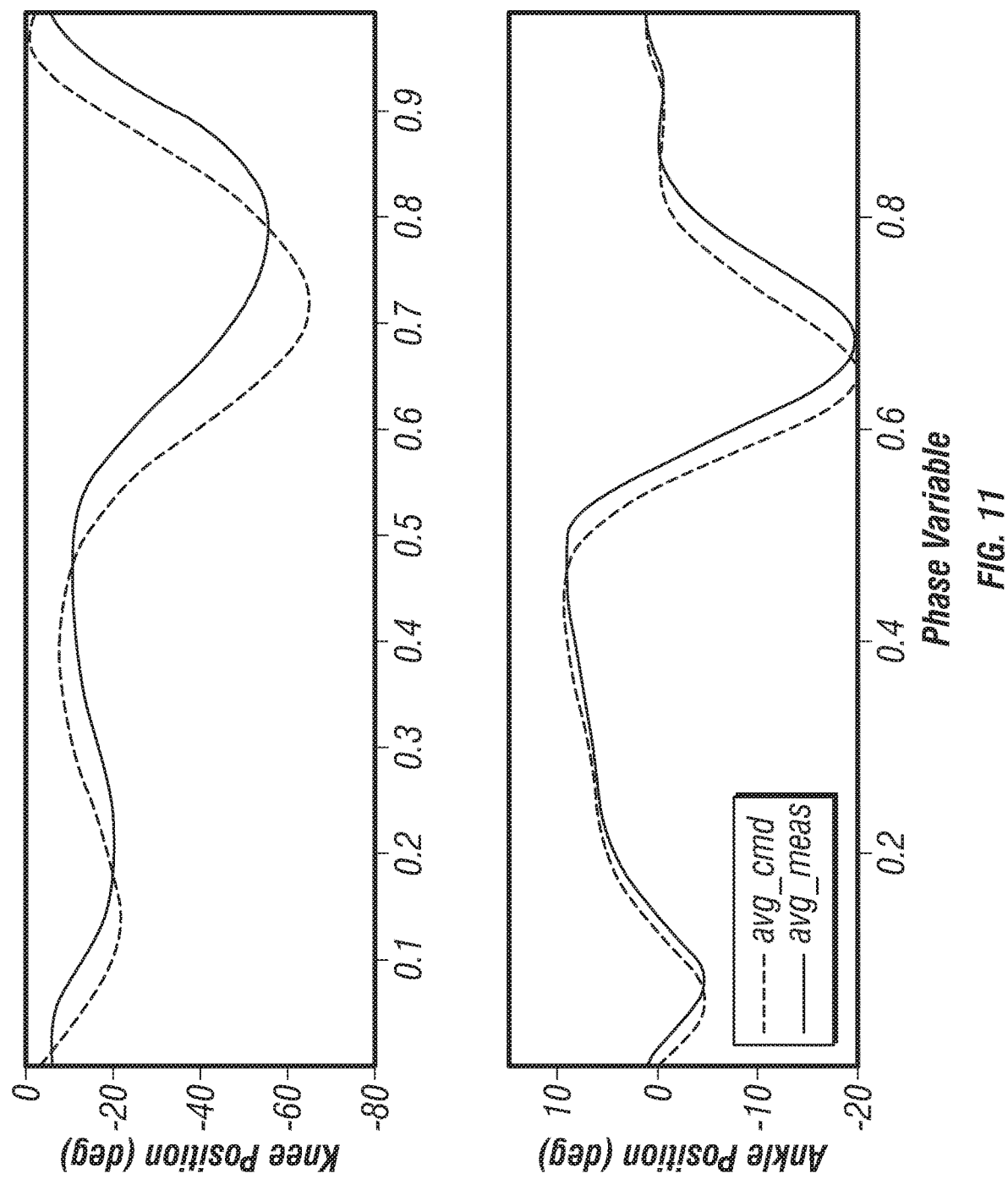
FIG. 11 illustrates plots of the tracking data from walking experiments utilizing exemplary embodiments at a constant speed.
Figure 12:
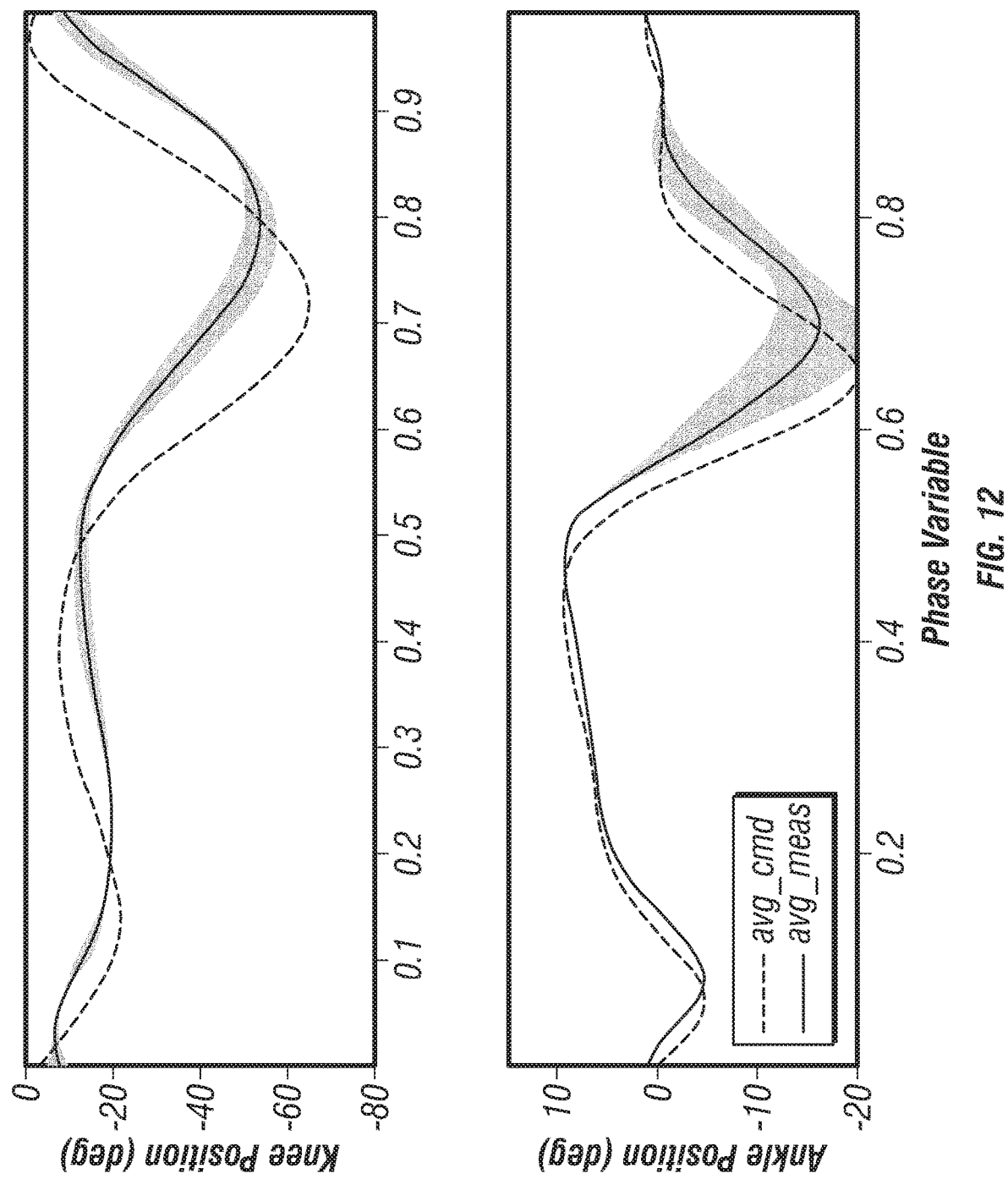
FIG. 12 illustrates a plot of the tracking data from walking experiments utilizing exemplary embodiments at various speeds.

FIG. 11 and FIG. 12 illustrate plots of the tracking data from walking experiments utilizing the embodiment of FIG. 9. In the illustrated plots, the "cmd" signal is the desired joint angle produced by the control strategy as a function of the phase variable measurement, which the motors attempt to track. The "meas" signal is the actual measured joint angle, demonstrating the ability of the prosthesis to track the commanded signal. The plots in FIG. 11 and FIG. 12 show the averaged signals over multiple walking steps on a treadmill. The shaded region represents +/−one standard deviation about the average. FIG. 11 illustrates results for walking at approximately 1 mile/hour. FIG. 12 illustrates walking at various speeds from 1 to 3 mile/hour, demonstrating the ability of the controller to automatically adjust walking speed based on measurements of the phase variable.

Figure 13:
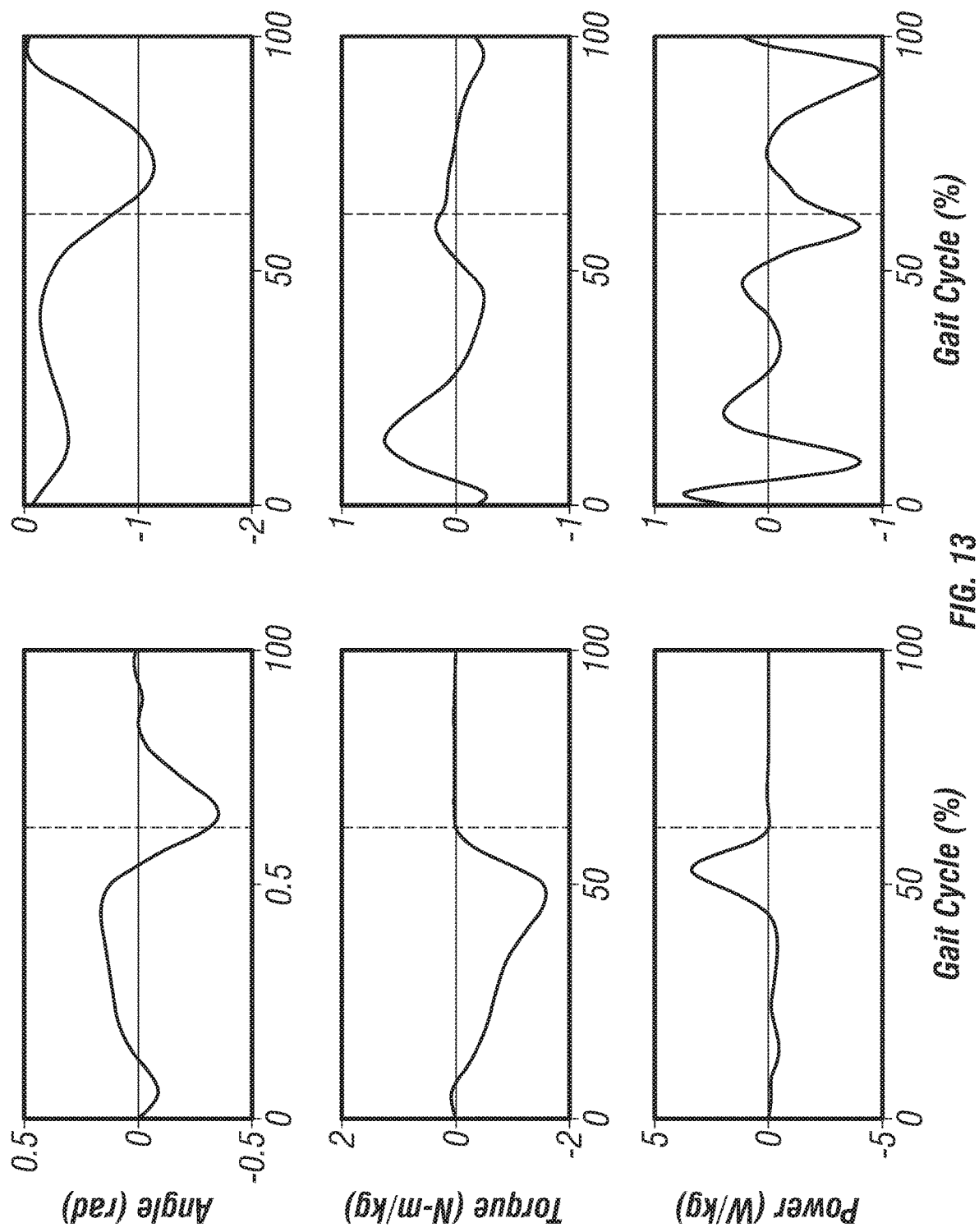
FIG. 13 illustrates empirical human gait data of the ankle and knee joints according to exemplary embodiments.

FIG. 13 illustrates empirical human gait data of the ankle (left column) and knee (right column) joints for able-bodied subjects at normal walking speeds. The left column plots indicate the empirical joint kinematics for the ankle, and the right column plots are for the knee. The top row illustrates the ankle and knee joint angles in radians, the middle row displays the joint torques in Nm per weight in kg, and the bottom row shows the joint mechanical power in Watts per weight in kg. Note, the vertical dashed line indicates the start of the swing period.

To evaluate the performance of the embodiment shown in FIG. 9, a linear proportional-derivative (PD) controller was implemented in position mode to control the leg joints individually. In other embodiments, a different controller may be used in the joint position control loop. The PD controller consist of a control law $u_{PD}=-K_P(\theta-\theta_d)-K_d\dot{\theta}$, where $\theta_d$ is the desired joint angular position, $\theta$ is the measured joint angular position, $\dot{\theta}$ is the measured joint angular velocity, $K_p$ is the proportional gain affecting the stiffness of the joint, and $K_d$ is the derivative gain behaving as a damping term. Step inputs were evaluated at each joint to obtain dynamic response characteristics to evaluate the performance of the system. A position step input of 10 degrees (0.1745 radians) was commanded separately for both knee and ankle (see left column of FIG. 14). Response characteristics were computed as follows (all times in seconds): rise time 0.917 (knee) 0.205 (ankle); peak time 2.57 (knee) 1.64 (ankle); settling time 1.48 (ankle). The ankle step response has better performance with faster response and settling time than the knee. Note the knee's actuation system receives a larger inertia to overcome with the opposing moment due to the mass of the leg during free swing. Thus, the knee has a slower response time compared to the ankle, where the settling time could not be computed based on the undershoot response. Control gains were selected for stable responses. Gains were increased to improve the control response of the knee, but under disturbances it proved to be unstable.

Figure 14:
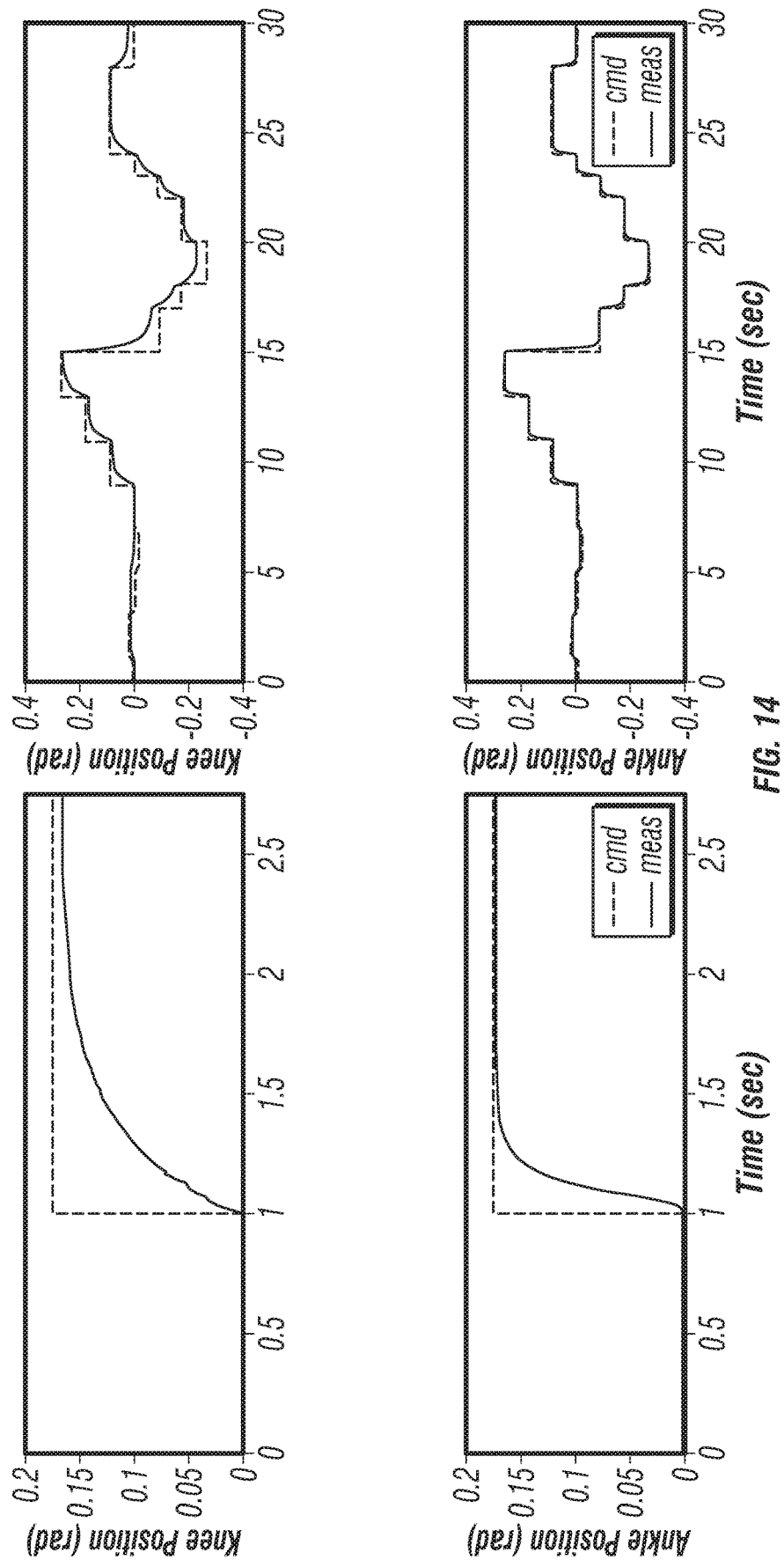
FIG. 14 illustrates knee and ankle angular position step response according to exemplary embodiments.

A step duty cycle was commanded to both joints individually to evaluate transient responses during small time durations (see right column of FIG. 14). The desired position commands applied in order were [0, 0.01745, 0, −0.01745, 0, 0.08727, 0.1745, 0.2618, −0.08727, −0.1745, −0.2618, −0.1745, −0.08727, 0, 0.08727, 0 radians] at various time intervals over time length of 30 seconds. Again the ankle actuator was able to meet the desired commanded position, while the knee had steady-state error due to its undershoot behavior response. However, experimentation with the leg attached to amputees, an aided torque will be applied to the knee joint due to the moment created from the thigh motion during swing period. While these results are preliminary bench top testing, future work may entail performing system identification techniques to accurately determine the bandwidth of each actuator. It is important to note it may potentially be a destructive test, particularly for the knee, if a full spectrum analysis is to be performed.

To implement advance control methods for a powered prosthetic leg, it's important to have a fast, real-time control processor to compute the algorithms efficiently and effectively for experimentation purposes with minimal processing delay. Other robotic systems have had success using real-time control for their algorithms, especially on bipedal robots like ATRIAS [32] and MABEL [33]. The real-time control interface chosen for the prosthetic leg is a dSPACE DS1007, where both real-time control and data acquisition are performed. All electronic signals from the leg are sent to the dSPACE processor board for computation and are monitored real-time using a PC with dSPACE ControlDesk Next Generation software. The control algorithms are programmed using MATLAB/Simulink (Version: 2013b, The Mathworks, Natick, Mass., USA). Furthermore, safety conditions were placed with software logic and emergency stop button to safely operate the leg in case a failure was to occur.

The main areas in implementing the control algorithms for the leg include, but not limited to, the virtual constraints, the phase variable, the sensors signal processing/filtering, and the kinematic analysis for torque calculations in performing closed-loop torque control. The virtual constraints were designed offline from empirical able-bodied walking gaits ([24] and FIG. 13) and programmed in MATLAB/Simulink to interface with dSPACE. The overall controller implemented to operate the leg to produce preliminary results was a PD control law using the previously-defined virtual constraints:

$$u_{PD} = -K_p(H_{0P_qP} - h_P^d(s_P)) - K_d(H_{0P_qP}), \quad (15)$$

where as before Kp and Kd are gains to control stiffness and damping in the system, respectively. The proposed phase variable sP is based on previous work of finding a robust parameterization of human locomotion from the hip phase angle [35]. Results from human subjects have shown that this approach produces a monotonic and bounded phase variable, even during perturbation. Experiments were performed using motion capture cameras (Vicon, Oxford, UK) in collecting kinematic data of human walking over a walkway with a perturbation mechanism. The phase variable was computed offline by post processing the kinematic data. A major challenge was recreating results from post processed data to real-time computation of the phase variable.

The first step for the control algorithms was producing the phase variable algorithms for real-time measurements. Serial communication for the IMU sensor were developed to output Euler Angles at a sample rate of 500 Hz, and the sensor is mounted along the human's thigh in the sagittal plane measuring the human's hip angle. Eq. 16 presents the normalized phase variable function based on the hip phase angle [35]:

$$s_P = \frac{\operatorname{atan2}(z(\tilde{\phi} + \tilde{\gamma}) \cdot \phi + \gamma)}{2\pi}, \quad (16)$$

where $$z = \frac{|\phi_{max} - \phi_{min}|}{|\tilde{\phi}_{max} - \tilde{\phi}_{min}|},$$

$$\gamma = -\left(\frac{\phi_{max} + \phi_{min}}{2}\right), \tilde{\gamma} = -\left(\frac{\tilde{\phi}_{max} + \tilde{\phi}_{min}}{2}\right)$$

$$\phi = \theta + \delta, \tilde{\phi} = \int_0^\tau \phi(\tau) d\tau$$

Figure 15:
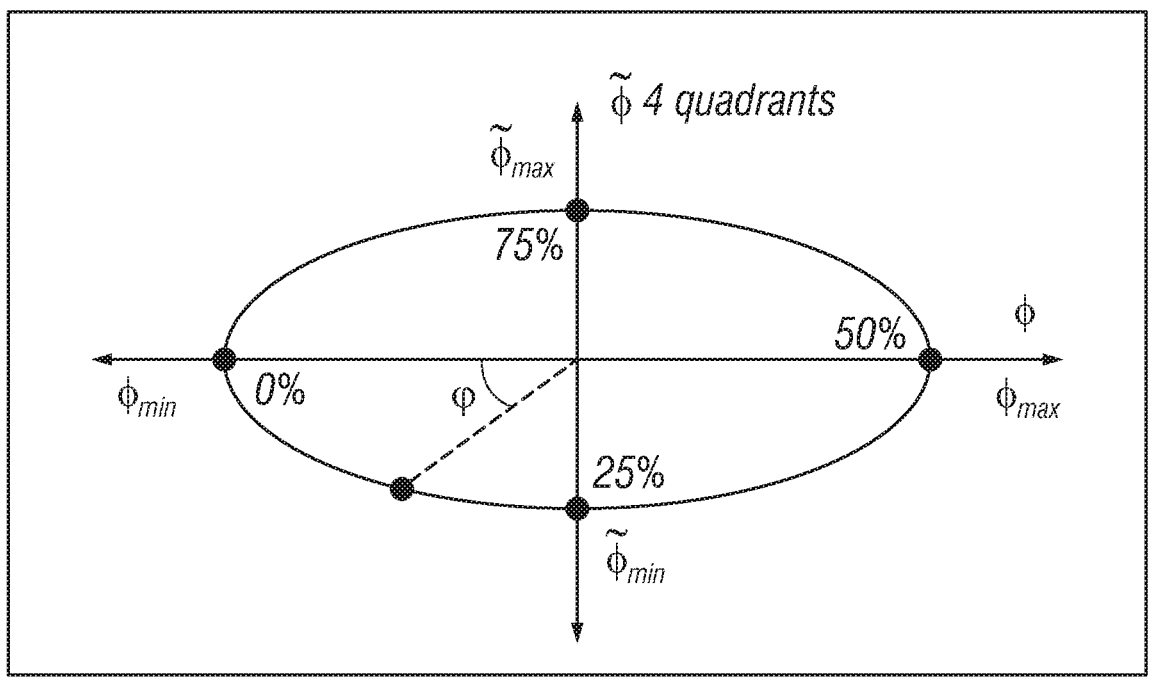
FIG. 15 illustrates a phase portrait of hip angle and hip velocity with the hip phase angle according to exemplary embodiments.

The variable θ is the hip angle with respect to the vertical/gravity. The variable δ is chosen such that $\int_0^T \phi(\tau) d\tau = \int_0^T (\theta(\tau) + \delta) d\tau = 0$, where T represents the total amount of time of a gait cycle. The variable z is referred to as the scale factor, and the variables γ and are what are known as the shift parameters for the hip position and integral, respectively. They are computed from the bounds of the derived phase portrait of the hip angle and integral. The phase variable is normalized from 0 to 2π (based on the orbit of the phase portrait) for a final range of zero to one. The maximum/minimum variables are computed based a four-quadrant window from the phase portrait. Equation 16 is the actual phase variable function as referenced in Eq. 13. FIG. 15 graphically displays the computed maximum/minimum values as the phase angle φ enters each quadrant (i.e. 0%, 25%, 50%, etc), where an updated maximum or minimum is computed for every passing quadrant of the phase portrait. In FIG. 15, the negative x-axis of quadrant 3 is considered 0% of the phase variable as it increases to a full counter-clockwise revolution to 100%. Each axis crossing of thy phase angle will contain either a maximum or minimum value of the hip angle or hip integral to determining the phase. In other embodiments, the phase may be calculated from the hip angle and hip velocity.

Several preliminary bench top testing were performed to verify the functionality of the unified controller operating on a powered prosthesis. Before operating the leg with the real-time computation of the phase variable, an ideal phase variable signal was constructed to observe how the virtual constraint performs from ideal conditions. The ideal phase variable was a monotonic, increasing linear signal from 0 to 1 to replicate a human walking from 0 to 100% gait cycle. This aided in determining initial control gains to program into the leg for experimentation with human subjects. Bench top testing entailed using a continuous, ideal phase variable for real-time control tuning.

Figure 16:
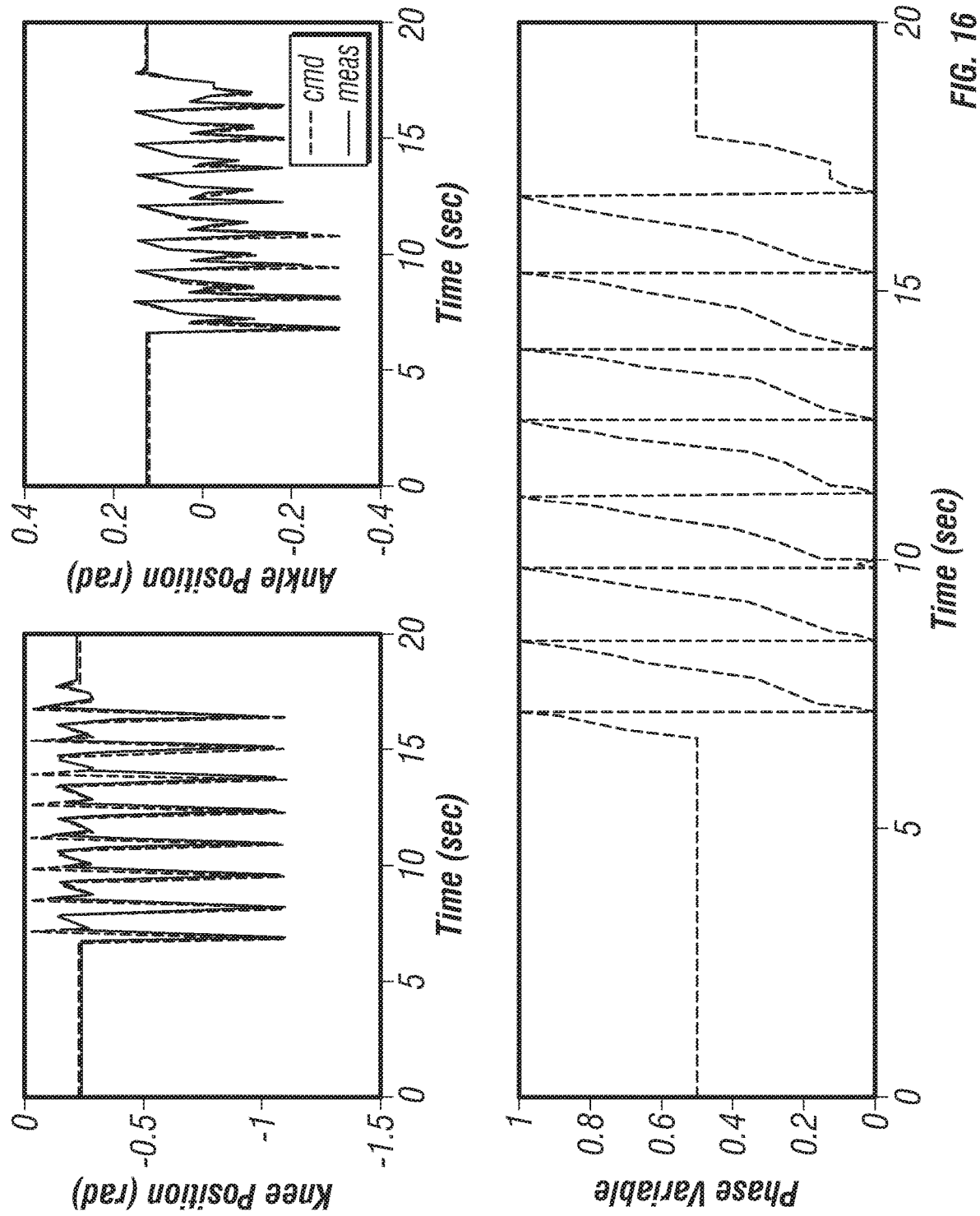
FIG. 16 illustrates experimental leg bench top data of a unified controller for a knee joint according to exemplary embodiments.

Once response showed low tracking error and adequate transient response, then the controller was switched to use actual real-time measurements of the phase variable. A start/stop bench top experiment was developed where the able-bodied subject began at a rest position, transition to continuous walking, and ended at rest. FIG. 16 illustrates experimental leg bench top results of unified controller for the knee joint (top left) and the ankle joint (top right) using actual phase variable measurements (bottom) from an able-bodied subject at slow walking speed 1.0 miles per hour on a treadmill. In the top two plots. the dotted line is the controller reference command and the solid line is the joint angle response output. In the bottom plot, the dashed line is the phase variable. The subject initiated walking after 6 seconds with stopping after the 18 second mark as illustrated in FIG. 16.

Notice the bottom plot in FIG. 16 that the phase variable is not exactly linear, however it is still monotonic, which is one of the required properties for using a phase variable for a virtual constraint controller. Recall the data in FIGS. 11 and 12 was collected using an exemplary embodiment of the prosethetic device disclosed in FIG. 9. In contrast, the data in FIG. 16 was collected with an ablebodied human walking on a treadmill (Model: Commercial 1750, NordicTrack, Chaska, Minn., USA) at 1.0 miles per hour (slow walking speed) wearing the IMU sensor while the leg is mounted fixed to a table. The human subject started from rest position, then turned on the treadmill to begin walking continuously, and eventually turned off the treadmill to end at rest. Overall, the leg tracked the response well for bench top testing. The leg inherently begins and ends at a stance position, where the knee has small flexion at safe phase variable mode of 0.5. This allows the leg to not collapse with large knee flexion, so the human subject will not fall down.

CONCLUSIONS

The development of a single, unified controller that captures the entire gait cycle eliminates the need to divide the gait into different periods, each with their own controllers. DFT methods were used to produce a unified virtual constraint for a feedback-linearizing controller based on a desired trajectory. While the feasibility of the controller was demonstrated using a walking gait in this embodiment, the DFT method approach can be applied equally well to other locomotion activities with well-characterized joint kinematics. For instance, the control strategy could be applied to different tasks, including for example, stair and slope ascent/descent.

The systems and methods described herein can be used to control other powered lower limb devices besides limb 10. The systems and methods described herein can be used to control a single joint powered lower limb device, such as an ankle prosthesis, or a multi joint powered lower limb device, such as limb 10, which includes a motorized ankle and a motorized knee.

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:
[1] K. Ziegler-Graham, E. J. MacKenzie, P. L. Ephraim, T. G. Travison, and R. Brookmeyer, "Estimating the prevalence of limb loss in the united states: 2005 to 2050," Archives of physical medicine and rehabilitation, vol. 89, no. 3, pp. 422-429, 2008.
[2] W. C. Miller, A. B. Deathe, M. Speechley, and J. Koval, "The influence of falling, fear of falling, and balance confidence on prosthetic mobility and social activity among individuals with a lower extremity amputation," Archives of physical medicine and rehabilitation, vol. 82, no. 9, pp. 1238-1244, 2001.
[3] R. S. Galley, M. A. Wenger, M. Raya, N. Kirk, K. Erbs, P. Spyropoulos, and M. S. Nash, "Energy expenditure of trans-tibial amputees during ambulation at self-selected pace," Prosthetics & Orthotics Int., vol. 18, no. 2, p. 84, 1994.
[4] F. Sup, A. Bohara, and M. Goldfarb, "Design and control of a powered transfemoral prosthesis," The International journal of robotics research, vol. 27, no. 2, pp. 263-273, 2008.
[5] R. D. Bellman, M. A. Holgate, and T. G. Sugar, "Sparky 3: Design of an active robotic ankle prosthesis with two actuated degrees of freedom using regenerative kinetics," in Biomedical Robotics and Biomechatronics, 2008. BioRob 2008. 2nd IEEE RAS & EMBS International Conference on. IEEE, 2008, pp. 511-516.
[6] S. K. Au and H. Herr, "Powered ankle-foot prosthesis," Robotics & Automation Magazine, IEEE, vol. 15, no. 3, pp. 52-59, 2008.
[7] F. Sup, H. A. Varol, and M. Goldfarb, "Upslope walking with a powered knee and ankle prosthesis: initial results with an amputee subject," Neural Systems and Rehabilitation Engineering, IEEE Transactions on, vol. 19, no. 1, pp. 71-78, 2011.
[8] N. P. Fey, A. Simon, A. J. Young, and L. J. Hargrove, "Controlling knee swing initiation and ankle plantarflexion with an active prosthesis on level and inclined surfaces at variable walking speeds," Translational Engineering in Health and Medicine, IEEE Journal of, vol. 2, pp. 1-12, 2014.
[9] M. F. Eilenberg, H. Geyer, and H. Herr, "Control of a powered ankle-foot prosthesis based on a neuromuscular model," Neural Systems and Rehabilitation Engineering, IEEE Transactions on, vol. 18, no. 2, pp. 164-173, 2010.
[10] A. M. Simon, K. A. Ingraham, N. P. Fey, S. B. Finucane, R. D. Lipschutz, A. J. Young, and L. J. Hargrove, "Configuring a powered knee and ankle prosthesis for transfemoral amputees within five specific ambulation modes," PloS one, vol. 9, no. 6, p. e99387, 2014.
[11] A. Isidori, Nonlinear Control Systems, 3rd ed. London, England: Springer, 1995.
[12] A. E. Martin, D. C. Post, and J. P. Schmiedeler, "Design and experimental implementation of a hybrid zero dynamics-based controller for planar bipeds with curved feet," The International Journal of Robotics Research, vol. 33, no. 7, pp. 988-1005, 2014.
[13] K. Sreenath, H.-W. Park, I. Poulakakis, and J. W. Grizzle, "A compliant hybrid zero dynamics controller for stable, efficient and fast bipedal walking on mabel," The International Journal of Robotics Research, vol. 30, no. 9, pp. 1170-1193, 2011.
[14] R. D. Gregg, E. J. Rouse, L. J. Hargrove, and J. W. Sensinger, "Evidence for a time-invariant phase variable in human ankle control," PLoS ONE, vol. 9, no. 2, p. e89163, 2014, doi: 10.1371/journal.pone.0089163.
[15] R. D. Gregg and J. W. Sensinger, "Biomimetic virtual constraint control of a transfemoral powered prosthetic leg," in American Control Conference (ACC), 2013. IEEE, 2013, pp. 5702-5708.
[16] R. D. Gregg, T. Lenzi, L. J. Hargrove, and J. W. Sensinger, "Virtual constraint control of a powered prosthetic leg: From simulation to experiments with transfemoral amputees," IEEE Trans. Robotics, 2014, in press.
[17] R. D. Gregg, T. Lenzi, N. P. Fey, L. J. Hargrove, and J. W. Sensinger, "Experimental effective shape control of a powered transfemoral prosthesis," in IEEE Int. Conf. Rehab. Robotics, Seattle, Wash., 2013.
[18] A. E. Martin and R. D. Gregg, "Hybrid Invariance and Stability of a Feedback Linearizing Controller for Powered Prostheses," in American Control Conference, 2015, submitted.
[19] A. H. Hansen, D. S. Childress, and E. H. Knox, "Roll-over shapes of human locomotor systems: Effects of walking speed," Clinical Biomechanics, vol. 19, no. 4, pp. 407-14, 2004.
[20], "Prosthetic foot roll-over shapes with implications for alignment of trans-tibial prostheses," Prosthetics and Orthotics International, vol. 24, no. 3, pp. 205-15, 2000.
[21] A. E. Martin and J. P. Schmiedeler, "Predicting human walking gaits with a simple planar model," Journal of Biomechanics, vol. 47, no. 6, pp. 1416-21, 2014.

[22] R. M. Murray, Z. Li, and S. S. Sastry, A Mathematical Introduction to Robotic Manipulation, 1st ed. Boca Raton, Fla.: CRC Press, 1994.

[23] E. R. Westervelt, J. W. Grizzle, C. Chevallereau, J. H. Choi, and B. Morris, Feedback Control of Dynamic Bipedal Robot Locomotion. Boca Raton, Fla.: CRC Press, 2007.

[24] D. Winter, Biomechancis and Motor Control of Human Movement. Hoboken, N.J.: John Wiley and Sons. Inc, 2009.

[25] A. V. Oppenheim, R. W. Schafer, J. R. Buck, et al., Discrete-Time Signal Processing. Upper Saddle River, N.J.: Prentice-Hall Englewood Cliffs, 1989, vol. 2.

[26] A. D. Poularikas, Transforms and Applications Handbook. Boca Raton, Fla.: CRC press, 2009.

[27] R. G. Lyons, Understanding Digital Signal Processing. Pearson Education, 2010.

[28] W. L. Briggs et al., The DFT: An Owners' Manual for the Discrete Fourier Transform. Philadelphia, Pa.: Siam, 1995.

[29] J. Perry and J. Burnfield, Gait Analysis: Normal and Pathological Function. Thorofare, N.J.: Slack-Incorporated, 2010.

[30] T. Bennett, R. Jafari, and N. Gans, "An extended kalman filter to estimate human gait parameters and walking distance," in American Control Conference (ACC), 2013. IEEE, 2013, pp. 752-757.

[31] D. J. Villarreal and R. D. Gregg, "A survey of phase variable candidates of human locomotion," in IEEE Engineering in Medicine and Biology Conference, Chicago, Ill., August 2014.

[32] S. Kolathaya and A. D. Ames, "Achieving bipedal locomotion on rough terrain through human-inspired control," presented at the IEEE Int. Symp. Safety Security Rescue Robot. College Station, Tex., USA, 2012

[33] A. Ramezani, J. W. Hurst, K. A. Hamed, and J. W. Grizzle, "Performance analysis and feedback control of ATRIAS, a 3D bipedal robot," ASME J. Dyn. Syst. Meas. Control, vol. 136, no. 2, p. 021012, 2013.

[34] A. Simon, N. Fey, S. Finucane, R. Lipschutz, and L. Hargrove, "Strategies to reduce the configuration time for a powered knee and ankle prosthesis across multiple ambulation modes," presented at the IEEE Int. Conf. Rehab. Robotics, Seattle, Wash., USA, 2013.

[35] D. J. Villarreal, H. Poonawala, and R. D. Gregg. A Robust Parameterization of Human Joint Patterns Across Phase-Shifting Perturbations. IEEE Trans Neural Sys and Rehab Eng, 2015, under review.

The invention claimed is:

1. A method for controlling a prosthetic device, the method comprising:
   measuring a plurality of variables with one or more sensors, wherein:
      the one or more sensors are operatively coupled to a controller; and
      the controller is configured to control the prosthetic device comprising a plurality of joint elements;
   determining a value of a monotonic phasing variable based on measurements of the plurality of variables; and
   adjusting a joint element of the plurality of joint elements in response to the value of the monotonic phasing variable by enforcing a unified virtual constraint that controls an entire gait cycle of the prosthetic device, wherein the monotonic phasing variable is monotonic throughout the entire gait cycle.

2. The method of claim 1 wherein the monotonic phasing variable is a hip position of a user of the prosthetic device.

3. The method of claim 1 wherein the monotonic phasing variable is a hip phase angle of a user of the prosthetic device.

4. The method of claim 1 wherein the monotonic phasing variable is a location of a center of mass of a user of the prosthetic device.

5. The method of claim 1 wherein the entire gait cycle is an ambulatory cycle.

6. The method of claim 5 wherein the ambulatory cycle is a walking cycle.

7. The method of claim 5 wherein the ambulatory cycle is a running cycle.

8. The method of claim 5 wherein the ambulatory cycle is a stair climbing cycle.

9. The method of claim 1 wherein the unified virtual constraint is created utilizing a Discrete Fourier Transform (DFT).

10. The method of claim 1 wherein the unified virtual constraint is created utilizing a polynomial regression fit.

11. The method of claim 1 wherein the joint element of the plurality of joint elements comprises a knee joint.

12. The method of claim 1 wherein the joint element of the plurality of joint elements comprises an ankle joint.

13. The method of claim 1 wherein the plurality of joint elements comprises a knee joint and an ankle joint.

14. The method of claim 1 wherein the plurality of variables comprises an angle of a knee joint.

15. The method of claim 1 wherein the plurality of variables comprises a velocity of a knee joint.

16. The method of claim 1 wherein the plurality of variables comprises an angle of an ankle joint.

17. The method of claim 1 wherein the plurality of variables comprises a velocity of an ankle joint.

18. The method of claim 1 wherein the entire gait cycle comprises a stance phase and a swing phase.

19. The method of claim 18 wherein different control parameters are used for the stance phase and the swing phase to enforce the unified virtual constraint for the entire gait cycle of the prosthetic device.

20. A control system comprising:
   a plurality of sensors configured to measure a plurality of variables relating to a prosthetic device; and
   a controller operatively coupled to the plurality of sensors, wherein the controller is configured to:
      determine a value of a monotonic phasing variable based on measurements of the plurality of variables; and
      adjust a joint element of the prosthetic device in response to the value of the monotonic phasing variable by enforcing a unified virtual constraint that controls an entire gait cycle of the prosthetic device, wherein the monotonic phasing variable is monotonic throughout the entire gait cycle.

21. The control system of claim 20 wherein the monotonic phasing variable is a hip position of a user of the prosthetic device.

22. The control system of claim 20 wherein the monotonic phasing variable is a hip phase angle of a user of the prosthetic device.

23. The control system of claim 20 wherein the monotonic phasing variable is a location of a center of mass of a user of the prosthetic device.

24. The control system of claim 20 wherein the entire gait cycle is an ambulatory cycle.

25. The control system of claim 24 wherein the ambulatory cycle is a walking cycle.

26. The control system of claim 24 wherein the ambulatory cycle is a running cycle.

27. The control system of claim 24 wherein the ambulatory cycle is a stair climbing cycle.

28. The control system of claim 20 wherein the unified virtual constraint is created utilizing a Discrete Fourier Transform (DFT).

29. The control system of claim 20 wherein the unified virtual constraint is created utilizing a polynomial regression fit.

30. The control system of claim 20 wherein the joint element comprises a knee joint.

31. The control system of claim 20 wherein the joint element comprises an ankle joint.

32. The control system of claim 20 wherein the plurality of joint elements comprises a knee joint and an ankle joint.

33. The control system of claim 20 wherein the plurality of variables comprises an angle of a knee joint.

34. The control system of claim 20 wherein the plurality of variables comprises an angle of an ankle joint.

35. The control system of claim 20 wherein the entire gait cycle comprises a stance phase and a swing phase.

36. The control system of claim 35 wherein the system further comprises different control parameters for the stance phase and the swing phase to enforce the unified virtual constraint for the entire gait cycle of the prosthetic device.

37. A prosthetic device comprising:
a plurality of sensors configured to measure a plurality of variables relating to the prosthetic device; and
a controller operatively coupled to the plurality of sensors, wherein the controller is configured to:
determine a value of a monotonic phasing variable based on measurements of the plurality of variables; and
adjust a joint element of the prosthetic device in response to the value of the monotonic phasing variable by enforcing a unified virtual constraint that controls an entire gait cycle of the prosthetic device, wherein the monotonic phasing variable is monotonic throughout the entire gait cycle.

38. The prosthetic device of claim 37 wherein the monotonic phasing variable is a hip position of a user of the prosthetic device.

39. The prosthetic device of claim 37 wherein the monotonic phasing variable is a hip phase angle of a user of the prosthetic device.

40. The prosthetic device of claim 37 wherein the monotonic phasing variable is a location of a center of mass of a user of the prosthetic device.

41. The prosthetic device of claim 37 wherein the entire gait cycle is an ambulatory cycle.

42. The prosthetic device of claim 41 wherein the ambulatory cycle is a walking cycle.

43. The prosthetic device of claim 41 wherein the ambulatory cycle is a running cycle.

44. The control system of claim 41 wherein the ambulatory cycle is a stair climbing cycle.

45. The prosthetic device of claim 37 wherein the unified virtual constraint is created utilizing a Discrete Fourier Transform (DFT).

46. The prosthetic device of claim 37 wherein the unified virtual constraint is created utilizing a polynomial regression fit.

47. The prosthetic device of claim 37 wherein the joint element comprises a knee joint.

48. The prosthetic device of claim 37 wherein the joint element comprises an ankle joint.

49. The prosthetic device of claim 37 wherein the plurality of joint elements comprises a knee joint and an ankle joint.

50. The prosthetic device of claim 37 wherein the plurality of variables comprises an angle of a knee joint.

51. The prosthetic device of claim 37 wherein the plurality of variables comprises an angle of an ankle joint.

52. The prosthetic device of claim 37 wherein the plurality of variables comprises a velocity of a knee joint.

53. The prosthetic device of claim 37 wherein the plurality of variables comprises a velocity of an ankle joint.

54. The prosthetic device of claim 37 wherein the entire gait cycle comprises a stance phase and a swing phase.

55. The prosthetic device of claim 54 wherein the system further comprises different control parameters for the stance phase and the swing phase to enforce the unified virtual constraint for the entire gait cycle of the prosthetic device.

* * * * *